(12) United States Patent
Tehrani et al.

(10) Patent No.: US 8,280,513 B2
(45) Date of Patent: Oct. 2, 2012

(54) DEVICE AND METHOD TO TREAT FLOW LIMITATIONS

(75) Inventors: Amir J. Tehrani, San Francisco, CA (US); Rose Province, San Jose, CA (US); David Ligon, San Francisco, CA (US)

(73) Assignee: RMX, LLC, San Francisco, CA (US)

( * ) Notice: Subject to any disclaimer, the term of this patent is extended or adjusted under 35 U.S.C. 154(b) by 1024 days.

(21) Appl. No.: 12/004,845

(22) Filed: Dec. 21, 2007

(65) Prior Publication Data
US 2008/0154330 A1 Jun. 26, 2008

Related U.S. Application Data

(60) Provisional application No. 60/876,632, filed on Dec. 22, 2006.

(51) Int. Cl.
*A61N 1/18* (2006.01)
(52) U.S. Cl. ............... 607/42; 607/20; 600/529
(58) Field of Classification Search .......... 607/20, 607/42; 600/529
See application file for complete search history.

(56) References Cited

U.S. PATENT DOCUMENTS

| | | | |
|---|---|---|---|
| 3,773,051 A | 11/1973 | Holcomb et al. | |
| 4,827,935 A | 5/1989 | Geddes et al. | |
| 4,830,008 A | 5/1989 | Meer | |
| 5,056,519 A | 10/1991 | Vince | |
| 5,146,918 A | 9/1992 | Kallok et al. | |
| 5,174,287 A | 12/1992 | Kallok et al. | |
| 5,190,036 A | 3/1993 | Linder | |
| 5,211,173 A | 5/1993 | Kallok et al. | |
| 5,215,082 A | 6/1993 | Kallok et al. | |
| 5,233,983 A | 8/1993 | Markowitz | |
| 5,265,604 A | 11/1993 | Vince | |
| 5,281,219 A | 1/1994 | Kallok | |
| 5,300,094 A | 4/1994 | Kallok et al. | |
| 5,423,327 A | 6/1995 | Clauson et al. | |
| 5,483,969 A | 1/1996 | Testerman et al. | |
| 5,485,851 A | 1/1996 | Erickson | |
| 5,522,862 A | 6/1996 | Testerman et al. | |
| 5,524,632 A | 6/1996 | Stein et al. | |
| 5,540,731 A | 7/1996 | Testerman | |
| 5,540,732 A | 7/1996 | Testerman | |
| 5,540,733 A | 7/1996 | Testerman et al. | |

(Continued)

FOREIGN PATENT DOCUMENTS

DE 112004001957 T5 8/2006

(Continued)

OTHER PUBLICATIONS

"Quadripolar Pacing Addresses Issues Without Moving Leads," *Diagnostic & Invasive Cardiology*, 1 page, Jun. 1, 2010, Scranton Gillette Communications.

Abraham, W., "Advances in Heart Failure Therapy in the Primary Care Context," *Medscape Family Medicine/Primary Care*, 7 pages, 2004.

Aiyar, H. et al, "Laparoscopic Implant Device for Intermuscular Electrodes," *IEEE-EMBC and CMBCC*, pp. 1167-1168, 1995.

(Continued)

*Primary Examiner* — Joseph Stoklosa
(74) *Attorney, Agent, or Firm* — Levine Bagade Han LLP

(57) ABSTRACT

A device and method for detecting and treating airflow limitations in a subject is provided. Levels of flow limited breathing may be differentiated. Obstruction versus flow limited breathing may be differentiated as well. The EMG complex characteristics may be used to detect obstruction or flow limited breathing. The power spectral density plot of the EMG may be used to detect obstruction or flow limited breathing.

48 Claims, 12 Drawing Sheets

U.S. PATENT DOCUMENTS

| | | |
|---|---|---|
| 5,546,952 A | 8/1996 | Erickson |
| 5,549,655 A | 8/1996 | Erickson |
| 5,572,543 A | 11/1996 | Heinemann et al. |
| 5,678,535 A | 10/1997 | DiMarco |
| 5,766,228 A | 6/1998 | Bonnet et al. |
| 5,797,923 A | 8/1998 | Aiyar et al. |
| 5,800,470 A | 9/1998 | Stein et al. |
| 5,814,086 A | 9/1998 | Hirschberg et al. |
| 5,830,008 A | 11/1998 | Broschard, III |
| 5,876,353 A | 3/1999 | Riff |
| 5,895,360 A | 4/1999 | Christopherson et al. |
| 5,911,218 A | 6/1999 | DiMarco |
| 5,944,680 A | 8/1999 | Christopherson et al. |
| 6,021,352 A | 2/2000 | Christopherson et al. |
| 6,099,479 A | 8/2000 | Christopherson et al. |
| 6,212,435 B1 | 4/2001 | Lattner et al. |
| 6,224,562 B1 | 5/2001 | Lurie et al. |
| 6,251,126 B1 | 6/2001 | Ottenhoff et al. |
| 6,269,269 B1 | 7/2001 | Ottenhoff et al. |
| 6,312,399 B1 | 11/2001 | Lurie et al. |
| 6,314,324 B1 | 11/2001 | Lattner et al. |
| 6,345,202 B2 * | 2/2002 | Richmond et al. .............. 607/42 |
| 6,415,183 B1 | 7/2002 | Scheiner et al. |
| 6,463,327 B1 | 10/2002 | Lurie et al. |
| 6,480,733 B1 | 11/2002 | Turcott |
| 6,489,447 B1 | 12/2002 | Basey et al. |
| 6,512,949 B1 | 1/2003 | Combs et al. |
| 6,527,729 B1 | 3/2003 | Turcott |
| 6,542,774 B2 | 4/2003 | Hill et al. |
| 6,572,543 B1 | 6/2003 | Christopherson et al. |
| 6,574,507 B1 | 6/2003 | Bonnet |
| 6,587,725 B1 | 7/2003 | Durand et al. |
| 6,587,726 B2 | 7/2003 | Lurie et al. |
| 6,589,188 B1 | 7/2003 | Street et al. |
| 6,600,949 B1 | 7/2003 | Turcott |
| 6,633,779 B1 | 10/2003 | Schuler et al. |
| 6,651,652 B1 | 11/2003 | Ward |
| 6,731,984 B2 | 5/2004 | Cho et al. |
| 6,735,479 B2 | 5/2004 | Fabian et al. |
| 6,752,765 B1 | 6/2004 | Jensen et al. |
| 6,770,022 B2 | 8/2004 | Mechlenburg et al. |
| 6,811,537 B2 | 11/2004 | Bardy |
| 6,830,548 B2 | 12/2004 | Bonnet et al. |
| 6,881,192 B1 | 4/2005 | Park |
| 6,908,437 B2 | 6/2005 | Bardy |
| 7,058,453 B2 | 6/2006 | Nelson et al. |
| 7,070,568 B1 | 7/2006 | Koh et al. |
| 7,082,331 B1 | 7/2006 | Park et al. |
| 7,117,032 B2 | 10/2006 | Childre et al. |
| 7,277,757 B2 | 10/2007 | Casavant et al. |
| 7,532,934 B2 | 5/2009 | Lee et al. |
| 7,610,094 B2 * | 10/2009 | Stahmann et al. .............. 607/42 |
| 7,840,270 B2 | 11/2010 | Ignagni et al. |
| 7,970,475 B2 | 6/2011 | Tehrani et al. |
| 7,979,128 B2 | 7/2011 | Tehrani et al. |
| 8,116,872 B2 | 2/2012 | Tehrani et al. |
| 8,140,164 B2 | 3/2012 | Tehrani et al. |
| 2002/0049482 A1 | 4/2002 | Fabian et al. |
| 2002/0193697 A1 | 12/2002 | Cho et al. |
| 2002/0193839 A1 | 12/2002 | Cho et al. |
| 2003/0127091 A1 | 7/2003 | Chang |
| 2003/0153953 A1 | 8/2003 | Park et al. |
| 2003/0153954 A1 | 8/2003 | Park et al. |
| 2003/0153955 A1 | 8/2003 | Park et al. |
| 2003/0153956 A1 | 8/2003 | Park et al. |
| 2003/0195571 A1 | 10/2003 | Burnes et al. |
| 2003/0204213 A1 | 10/2003 | Jensen et al. |
| 2003/0225339 A1 | 12/2003 | Orr et al. |
| 2004/0044377 A1 * | 3/2004 | Larsson ........................ 607/42 |
| 2004/0059240 A1 | 3/2004 | Cho et al. |
| 2004/0077953 A1 | 4/2004 | Turcott |
| 2004/0088015 A1 | 5/2004 | Casavant et al. |
| 2004/0111040 A1 | 6/2004 | Ni et al. |
| 2004/0116784 A1 | 6/2004 | Gavish |
| 2004/0122484 A1 | 6/2004 | Hatlestad et al. |
| 2004/0134496 A1 | 7/2004 | Cho et al. |
| 2004/0138719 A1 | 7/2004 | Cho et al. |
| 2004/0176809 A1 | 9/2004 | Cho et al. |
| 2004/0199221 A1 | 10/2004 | Fabian et al. |
| 2004/0225226 A1 | 11/2004 | Lehrman et al. |
| 2004/0237963 A1 | 12/2004 | Berthon-Jones |
| 2005/0021102 A1 | 1/2005 | Ignagni et al. |
| 2005/0039745 A1 | 2/2005 | Stahmann et al. |
| 2005/0043644 A1 | 2/2005 | Stahmann et al. |
| 2005/0043772 A1 | 2/2005 | Stahmann et al. |
| 2005/0055060 A1 | 3/2005 | Koh et al. |
| 2005/0061315 A1 | 3/2005 | Lee et al. |
| 2005/0061319 A1 | 3/2005 | Hartley et al. |
| 2005/0061320 A1 | 3/2005 | Lee et al. |
| 2005/0065563 A1 | 3/2005 | Scheiner |
| 2005/0065567 A1 | 3/2005 | Lee et al. |
| 2005/0074741 A1 | 4/2005 | Lee et al. |
| 2005/0076909 A1 | 4/2005 | Stahmann et al. |
| 2005/0080461 A1 | 4/2005 | Stahmann et al. |
| 2005/0085734 A1 | 4/2005 | Tehrani |
| 2005/0085865 A1 * | 4/2005 | Tehrani .......................... 607/42 |
| 2005/0085866 A1 * | 4/2005 | Tehrani .......................... 607/42 |
| 2005/0085867 A1 * | 4/2005 | Tehrani et al. .................. 607/42 |
| 2005/0085868 A1 * | 4/2005 | Tehrani et al. .................. 607/42 |
| 2005/0085869 A1 * | 4/2005 | Tehrani et al. .................. 607/42 |
| 2005/0101833 A1 | 5/2005 | Hsu et al. |
| 2005/0107860 A1 | 5/2005 | Ignagni et al. |
| 2005/0115561 A1 | 6/2005 | Stahmann et al. |
| 2005/0119711 A1 | 6/2005 | Cho et al. |
| 2005/0145246 A1 | 7/2005 | Hartley et al. |
| 2005/0148897 A1 | 7/2005 | Cho et al. |
| 2005/0165457 A1 * | 7/2005 | Benser et al. ................... 607/42 |
| 2005/0224076 A1 | 10/2005 | Pfichner et al. |
| 2005/0240240 A1 | 10/2005 | Park et al. |
| 2005/0261600 A1 | 11/2005 | Aylsworth |
| 2005/0261747 A1 | 11/2005 | Schuler et al. |
| 2006/0030894 A1 | 2/2006 | Tehrani |
| 2006/0036294 A1 | 2/2006 | Tehrani |
| 2006/0058852 A1 * | 3/2006 | Koh et al. ....................... 607/42 |
| 2006/0064030 A1 | 3/2006 | Cosentino et al. |
| 2006/0064325 A1 | 3/2006 | Matsumoto et al. |
| 2006/0122622 A1 | 6/2006 | Truckai et al. |
| 2006/0122661 A1 | 6/2006 | Mandell |
| 2006/0122662 A1 | 6/2006 | Tehrani |
| 2006/0142815 A1 | 6/2006 | Tehrani et al. |
| 2006/0149334 A1 | 7/2006 | Tehrani et al. |
| 2006/0155341 A1 | 7/2006 | Tehrani et al. |
| 2006/0167523 A1 | 7/2006 | Tehrani et al. |
| 2006/0224211 A1 | 10/2006 | Durand et al. |
| 2006/0247729 A1 | 11/2006 | Tehrani et al. |
| 2006/0282131 A1 | 12/2006 | Caparso et al. |
| 2007/0021795 A1 | 1/2007 | Tehrani |
| 2007/0156199 A1 * | 7/2007 | Koh et al. ....................... 607/42 |
| 2008/0021506 A1 * | 1/2008 | Grocela .......................... 607/9 |
| 2008/0167695 A1 | 7/2008 | Tehrani et al. |
| 2008/0177347 A1 | 7/2008 | Tehrani et al. |
| 2008/0183239 A1 | 7/2008 | Tehrani et al. |
| 2008/0183240 A1 | 7/2008 | Tehrani et al. |
| 2008/0188903 A1 | 8/2008 | Tehrani et al. |
| 2008/0188904 A1 | 8/2008 | Tehrani et al. |
| 2008/0208281 A1 | 8/2008 | Tehrani et al. |
| 2011/0230932 A1 | 9/2011 | Tehrani et al. |

FOREIGN PATENT DOCUMENTS

| | | |
|---|---|---|
| DE | 112004001953 T5 | 10/2006 |
| DE | 112004001954 T5 | 10/2006 |
| WO | WO 86/00234 | 1/1986 |
| WO | WO 2005/037077 | 4/2005 |
| WO | WO 2005/037172 | 4/2005 |
| WO | WO 2005/037173 | 4/2005 |
| WO | WO 2005/037174 | 4/2005 |
| WO | WO 2005/037220 | 4/2005 |
| WO | WO 2005/037366 | 4/2005 |
| WO | WO 2007/058938 | 5/2007 |

OTHER PUBLICATIONS

Aiyar, H. et al, "Laparoscopic Implant Instrument for the Placement of Intramuscular Electrodes in the Diaphragm," *Transactions on Rehabilitation Engineering*, pp. 360-371, Sep. 1999.

Arzt, M. et al, "Treatment of Sleep Apnea in Heart Failure," *AJRCCM*, 36 pages, Mar. 9, 2006.

Bernardi, L. et al, "Effect of Rosary Prayer and Yoga Mantras on Autonomic Cardiovascular Rhythms: Comparative Study," *BMJ*, 323:22-29, Dec. 2001.

Bernardi, L. et al, "Slow Breathing Increases Arterial Baroreflex sensitivity in Patients with Chronic Heart Failure," *Circulation*, 105;143-145, 2002, *American Heart Association*.

Boston Scientific, "Diaphragm Stimulation During Daily LV Lead Impedance Measurements", Product Education Brochure, 2 pages, Sep. 26, 2008.

Bradley, T.D. et al, "Sleep Apnea and Heart Failure, Part I: Obstructive Sleep Apnea," *Circulation*, pp. 1671-1678, Apr. 1, 2003.

DiMarco, A F., "Combined intercostal and Diaphragm Pacing to Provide Artificial Ventilation in Patients With Tetraplegia" *Arch Phys Med Rehabil*, vol. (86), pp. 1200-1207, 2005.

DiMarco, A. F. et al, "Phrenic Nerve Pacing in a Tetraplegic Patient via Intramuscular Diaphragm Electrodes," *American Journal of Respiratory and Critical Care Medicine*, 144:1604-1606, 2002.

Dunn, R., "Diaphragm and Accessory Respiratory Muscle Stimulation Using Intramuscular Electrodes" *Arch Phys Med Rehabil*, vol. (76), pp. 266-271, 1995.

Fessler, H.E., "Heart-Lung Interactions: Applications in the Critically Ill," *Eur. Respir. J.*, vol. 10, pp. 226-237, 1997.

Fichter, J. et al, "Sleep-Related Breathing Disorders are Associate with Ventricular Arrhythmias in Patients with an Implantable Cardioverter-Defibrillator," *Chest*, vol. 122, pp. 558-561, Aug. 2002.

Garrigue, S. et al "Sleep Apnea: A New Indication for Cardiac Pacing?," *Pace*, vol. 27, pp. 204-211, Feb. 2004.

Glenn, W. W. L., "Diaphragm Pacing: Present Status," *PACE*, 1: 357-370, Jul.-Sep. 1978.

Glenn, W., et al. "Diaphragm Pacing" *Journal of Thoracic Cardiovascular Surgery*, vol. (75):2, pp. 273-281, 1978.

Gosselink, R. "Controlled Breathing and Dyspnea in Patients With Chronic Obstructive Pulmonary Disease," *Journal of Rehabilitaiton Research and Development*, 40(5):20-31, Supplement 2, Sep./Oct. 2003.

Harish, A. et al, "Laparoscopic Implant Device for Intramuscular Electrodes," *IEEE-EMBC and CMBCC*, 1167-1168, 1995.

Hayano, J. et al "Respiratory Sinus Arrhythmia: A Phenomenon Improving Pulmonary Gas Exchange and Circulatory Efficiency," *Circulation*, vol. 94, pp. 842-847, 1996.

Heinzer, R., et al, "Lung Volume and Continuous Positive Airway Pressure Requirements in Obstructive Sleep Apeau" *American Journal of Respiratory and Critical Care Medicine*, vol. 172, pp. 114-117, 2005.

Hennersdorf, M.G. et al, "Chemoreflexsensitivity in Chronic Heart Failure Patients," *European Journal of Heart Failure*, vol. 3, pp. 679-684, 2001.

Iazzo, P. ed., "Handbook of Cardiac Anatomy, Physiology, and Devices", p. 398, 2009.

Ishii, K. et al "Effects of Bilateral Transvenous Diaphragm Pacing on Hemodynamic Function in Patients after Cardiac Operations," *J Thorac Cardiovasc Surg*, vol. 100, pp. 108-114, 1990.

Javaheri, S. et al, "Sleep Apnea in 81 Ambulatory Male Patients with Stable Heart Failure: Types and Their Prevalences, Consequences, and Presentations," *Circulation*, vol. 97, pp. 2154-2159, 1998.

Jensen, A. et al, "Signal Transduction in Smooth Muscle: Airway caliber in healthy and asthmatic subjects effects of bronchial challenge and deep inspirations," *J. Appl Physiol*, 91:505-515, 2001.

Kohnlein, T, et al, "Central Sleep Apnea Syndrome in Patients with Chronic Heart Disease: a Critical Review of the Current Literature," *Thorax*, vol. 57, pp. 547-554, 2002.

Krachman, S. et al "Comparison of Oxygen Therapy with Nasal Continuous Positive Airway Pressure on Cheyne-Stokes Respiration During Sleep in Congestive Heart Failure," *Chest*, vol. 116, pp. 1550-1557, Dec. 1999.

LaFond, C. et al "Impact of CPAP on Asthmatic Patients with Obstructive Sleep Apnoea," *Eur Respir J*, vol. 29, pp. 307-311, 2007.

Lanfranchi, P.A. et al, "Prognostic Value of Nocturnal Cheyne-Stokes Respiration in Chonic Heart Failure," *Circulation*, pp. 1435-1440, 1999.

Leung, R. et al, "Sleep Apnea and Cardiovascular Disease," *Am J Respir Crit Care Med*, vol. 164, pp. 2147-2165, 2001.

Liem, L.B., "EP 101: Ventricular Tachycardia", EP Lab Digest, v.7, No. 8, Aug. 2007.

Malkin R. et al., "The Effect of Inducing Ventricular Fibrillation with 50-Hz Pacing Versus T are Stimulation on the Ability to Defibrillate", Pacing and Clinical Electrophysiology, vol. 21, issue 5, May 1998.

Mathew, O., "Effects of Transient Intrathoracic Pressure Changes (hiccups) on Systemic Arterial Pressure," *J Appl Physiol*, vol. 83, pp. 371-375, 1997.

Mitsuyana, T. et al, "Diaphragm Pacing With the Spinal Cord Stimulator," *Aeta Neurochir*, 87:89-92, 2003.

Norton, J., "Toward Consistent Definitions for Preload and Afterload," *Advan in Physiol Edu*. vol. 25, pp. 53-61, Mar. 2001.

Noshiro, M. et al., "Method of Electrophrenic Respiration for Producing a Natural Respiratory Flow Rate Using Feedback Control of Tidal Volume Waveform," *Med. & Bio. Eng. & Comput.*, 20:765-71, Nov. 1982.

Patroniti, M.D., et al "Sigh Improves Gas Exchange and Lung Volume in Patients with Acute Respiratory Distress Syndrome Undergoing Pressure Support Ventilation," *Anesthesiology*,96:788-794, 2002.

Peters, J. et al, "Negative Intrathoracic Pressue Decreases independently Left Ventricular Filling and Emptying," *American Physiological Society*, pp. H120-H131, 1989.

Pinsky, M. "Cardiovascular Issues in Respiratory Care," *Chest*, vol. 128, pp. 592-597, Nov. 2005.

Reeve, C., "New Implantable Breathing Device," University Hospitals of Cleveland, pp. 1-4, 2003.

Reeve, C., Christopher Reeve Paralysis Foundation Questions & Answers, pp. 1-3, Mar. 13, 2003.

Sauermann, S. et al, "Computer Aided Adjustment of the Phrenic Pacemaker: Automatic Functions. Documentation, and Quality Control," *Artificial Organs*, 21(3):216-217, 1997.

Schmit, B. D. et al, "Laparoscopic Placement of Electrodes for Diaphragm Pacing Using Stimulation to Locate the Phrenic Nerve Motor Points," *Transactions on Rehabilitation Engineering*, 6(4):382-390, Dec. 1998.

Schultz, R, et al "Nocturnal Periodic Breathing in Primary Pulmonary Hypertension," *Eur Respir J*, vol. 19, pp. 658-663, 2002.

Series, F. et al, "Assessment of Upper Airway Stabilizing Forces with the Use of Phrenic Nerve Stimulation in Conscious Humans," *J Appl Physiol*, vol. 94, pp. 2289-2295, 2003.

Series, F. et al, "Increasing the Functional Residual Capacity May Reverse Obstructive Sleep Apnea Sleep," 11(4):349-353, 1988.

Shaul, D.B. et al, "Thoracoscopic Placement of Phrenic Nerve Electrodes for Diaphragmatic Pacing in Children," *Journal of Pediatric Surgery*, 37:974-978, Jul. 2002.

Shier, D. et al, *Hole's Human Anatomy & Physiology*,pp. 798 (2 pages total), Jan. 6, 2009.

Simon, P. at al, "Vagal Feedback in the Entrainment of Respiration to Mechanical Ventilation in Sleeping Humans," *J. App. Physiol*, 89:760.769, 2000.

Sin, D. "Effects of Continuous Positive Airway Pressure on Cardiovascular Outcomes in Heart Failure Patients With and Without Cheyne-Stokes Respiration," *Circulation*, 102:61-66, Jul. 4, 2000.

Sorli, J. et al., "Ventilatory Assist Using Electrical Stimulation of AJdominal Muscles," *IEEE Transactions of Rehabilitation Engineering*, vol. 4, No. 1, pp. 1-6. Mar. 1996.

Taira. T. et al, "Phrenic Nerve Stimulation for Diaphragm Pacing With a Spinal Cord Stimulator," *Surg Neurol*. 59:128-132, 2003.

Van Houwelingen, K. et al "The Sleep Apnoea Syndromes," *European Heart Journal*, vol. 20, pp. 858-866, Jun. 1999.

Viasys Healthcare, "Ventilation Requires Perfect Balance", SensorMedics® 3100A HFOV, VIASYS Healthcare Brochure, 2 pages.

Wolk, R. et al "Sleep-Disordered Breathing and Cardiovascular Disease," *Circulation*, vol. 108, pp. 9-12, Jul. 2003.

Yim, S. et al "Continuous Positive Airway Pressure for Asthma: Not a Big Stretch?," *Eur Respir J*, vol. 29, pp. 226-228, 2007.

* cited by examiner

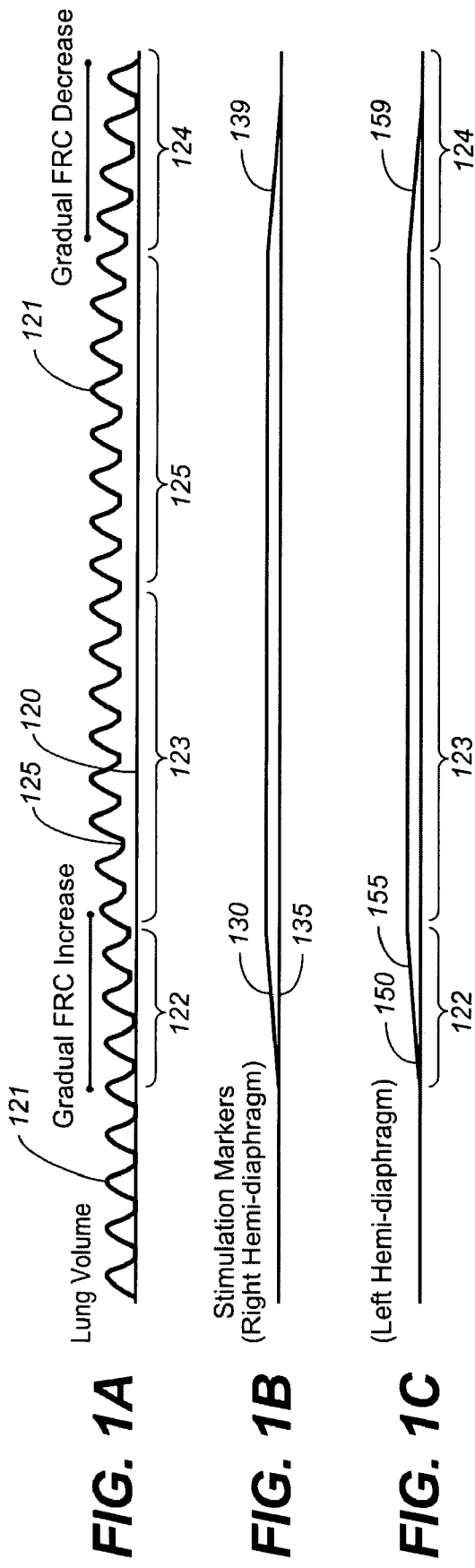

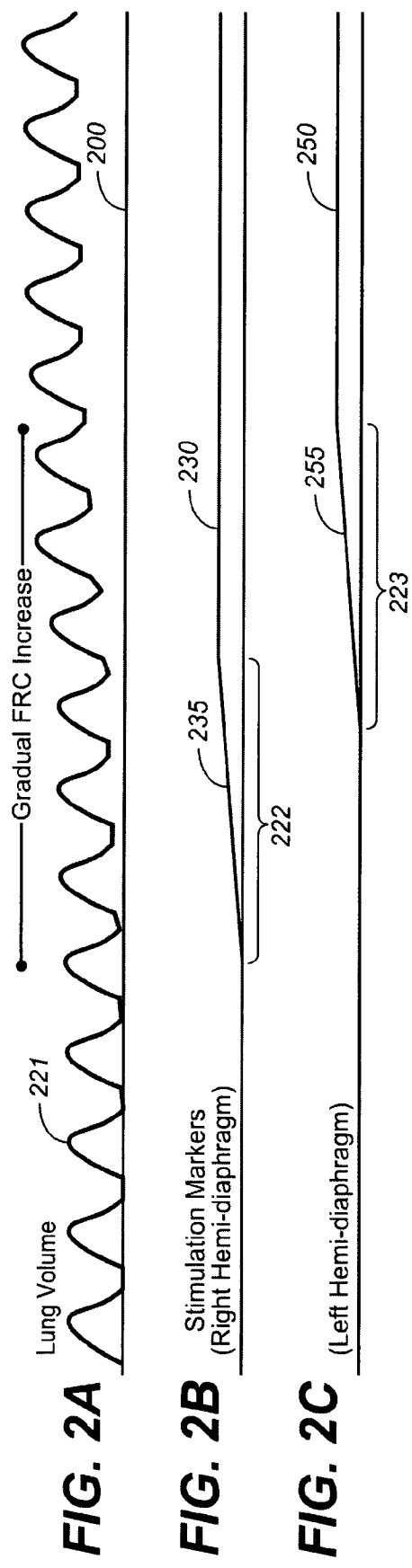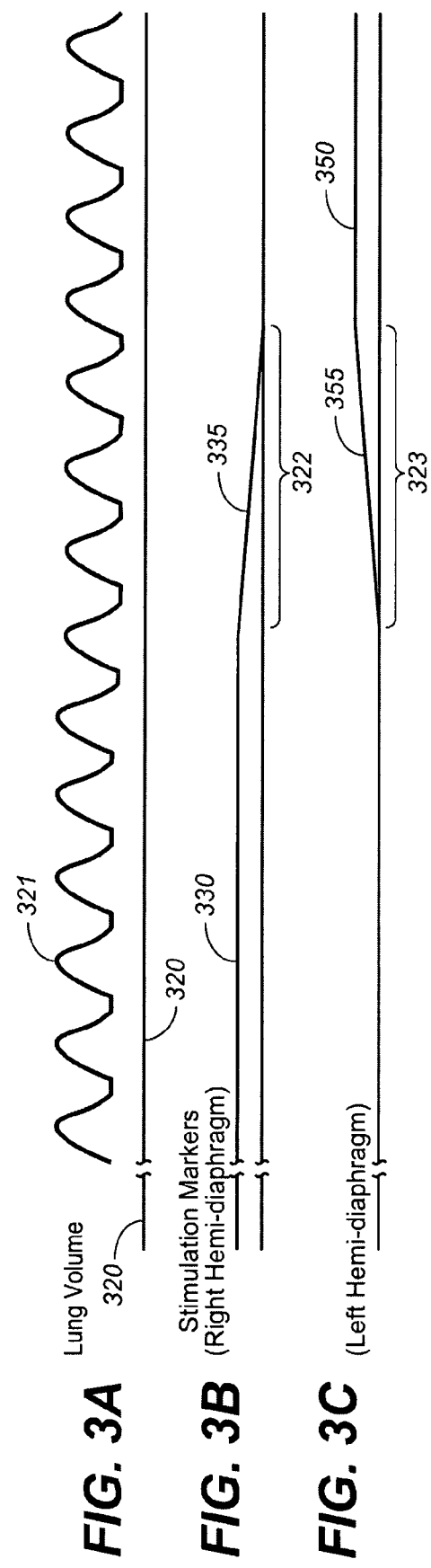

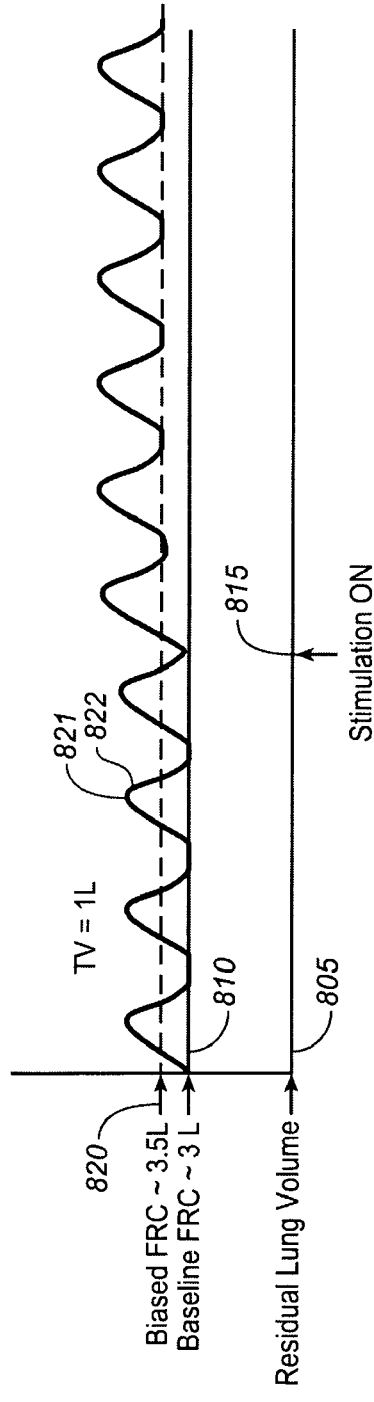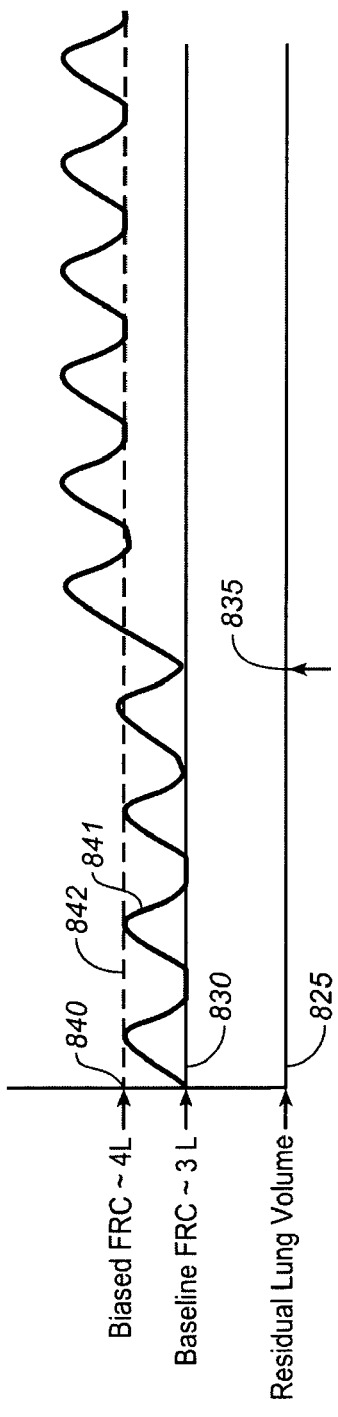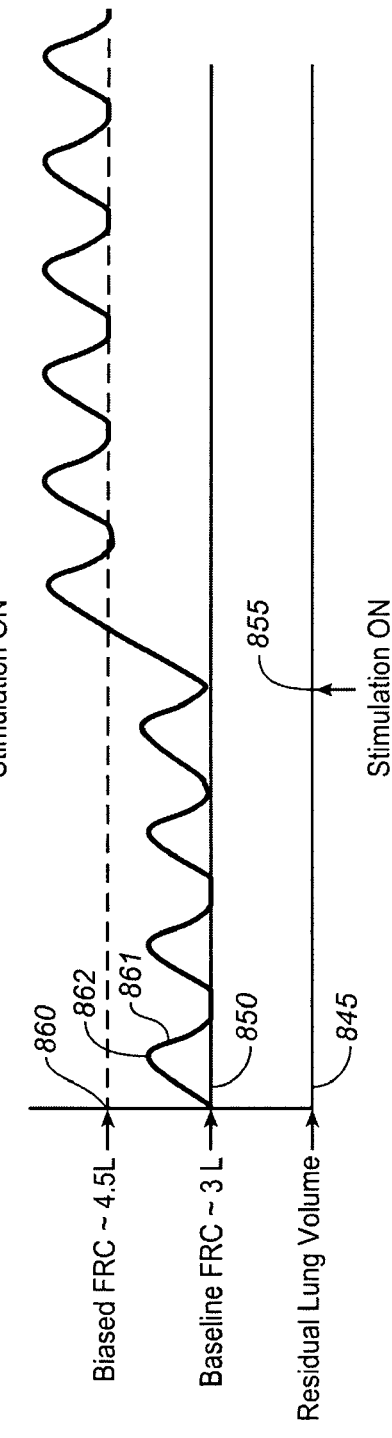

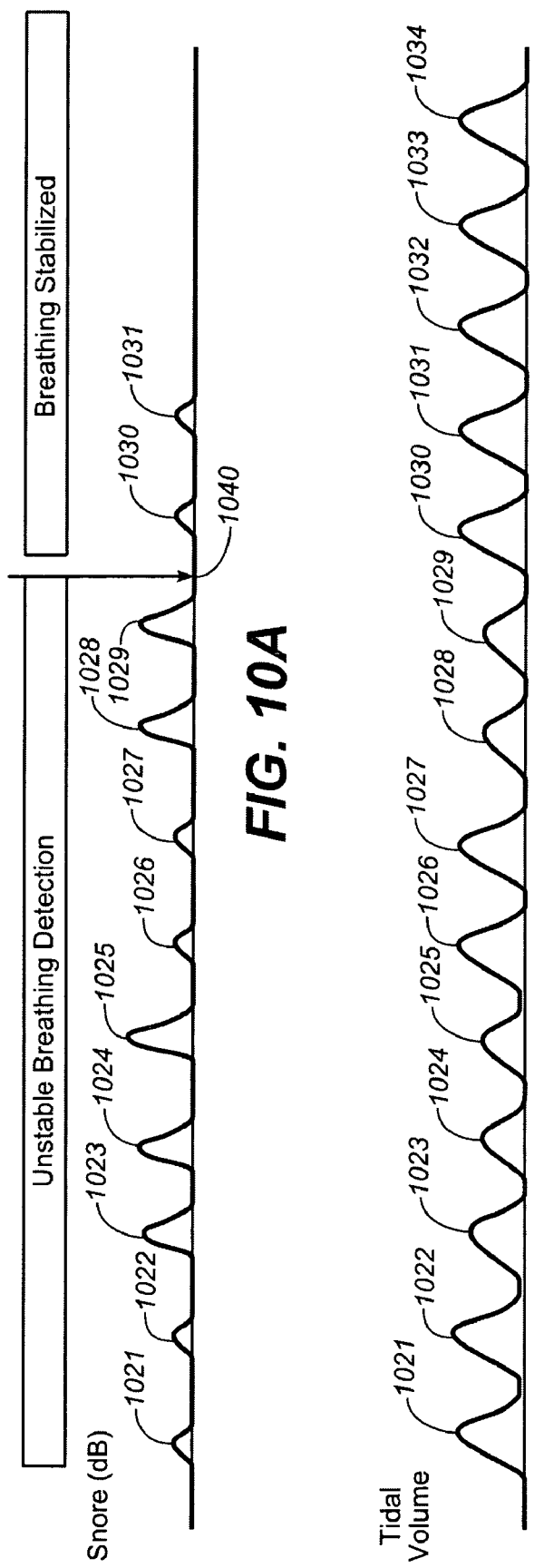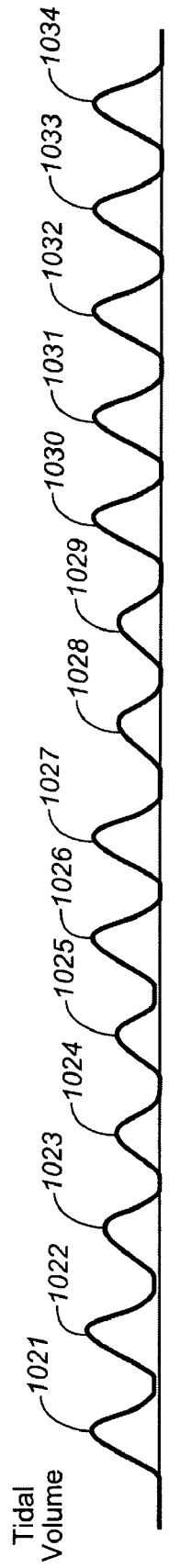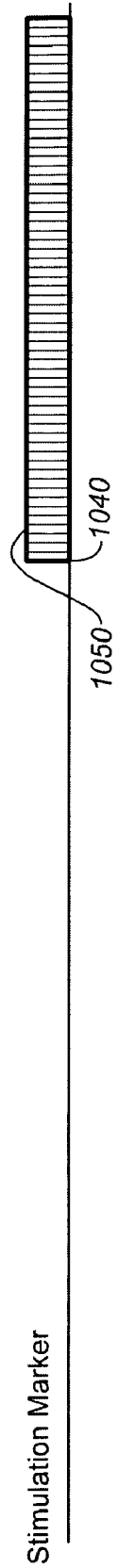

DEVICE AND METHOD TO TREAT FLOW LIMITATIONS

RELATED APPLICATION DATA

This application claims priority of U.S. Provisional Application Ser. No. 60/876,632 filed Dec. 22, 2006.

BACKGROUND

Devices and methods for creating a lung volume bias and/or increasing functional residual capacity have been disclosed in one or more of the following application: U.S. application Ser. No. 11/981,342 filed Oct. 31, 2007, which is a continuation in part of U.S. application Ser. No. 11/480,074 filed Jun. 29, 2006, which is a continuation in part of U.S. application Ser. No. 11/271,726 filed Nov. 10, 2005 which is a continuation in part of U.S. application Ser. No. 10/966,484 filed Oct. 15, 2004; U.S. application Ser. No. 10/966,474, filed Oct. 15, 2004; U.S. application Ser. No. 10/966,421, filed Oct. 15, 2004; and U.S. application Ser. No. 10/966,472 filed Oct. 15, 2004 which are continuations in part of U.S. application Ser. No. 10/686,891 filed Oct. 15, 2003 entitled: BREATHING DISORDER DETECTION AND THERAPY DELIVERY DEVICE AND METHOD all of which are incorporated herein by reference in their entirety. One or more of these applications also disclose a number of different applications for creating lung volume bias and/or increasing functional residual capacity.

SUMMARY

The present invention provides a device and method for providing electrical stimulation to elicit a diaphragm response. Among other things, one aspect of the invention provides a device and method for electrical stimulation to cause a lung volume bias. According to one aspect a lung volume bias augments lung volume during exhalation or inspiration and exhalation. According to one aspect, biased lung volume is superimposed on respiration. According to another aspect biased lung volume may be provided by causing a long slow increase in volume. According to one aspect the lung volume bias provides a therapeutic increase in airway traction. According to one aspect, lung volume bias provides a changing in lung volume over which intrinsic breathing may occur. In accordance with one aspect of the invention electrical stimulation may be provided directly or indirectly to the phrenic nerve and/or diaphragm of a subject. In accordance with one aspect of the invention treatment may be provided for a number of diseases, disorders and conditions that may relate to, have co-morbidities with, affect, be affected by respiratory or lung health status, respiration, ventilation, or blood gas levels. Such diseases and disorders may include but are not limited to obstructive respiratory disorders, upper airway resistance syndrome, snoring, obstructive apnea; central respiratory disorders, central apnea; hypopnea, hypoventilation, obesity hypoventilation syndrome other respiratory insufficiencies, inadequate ventilation or gas exchange, chronic obstructive pulmonary diseases; asthma; emphysema; chronic bronchitis; circulatory disorders; hemodynamic disorders; hypertension; heart disease; chronic heart failure; cardiac rhythm disorders; obesity or injuries in particular affecting breathing or ventilation.

Among other things, an aspect of the invention provides a device and method for electrical stimulation to increase functional residual capacity of a subjects lungs. Such increase in functional residual capacity according to one aspect may be a lung volume bias. The invention also provides a device and method for electrical stimulation to create caudal traction on the upper airway by increasing lung volume or functional residual capacity, thereby stabilizing the airway and/or improving upper airway patency. The invention also provides stimulation techniques for avoiding diaphragm fatigue, improving patient comfort, reducing undesired affects of stimulation such as upper airway closure, selecting stimulation parameters, selecting therapy type providing individualized treatment and/or diagnostics, adjusting stimulation, and/or improving battery life. The present invention also provides preventative or ameliorative treatment for diseases disorders or conditions. The present invention also provides improved stimulation for one or more diseases, disorders or conditions.

In accordance with one aspect of the invention slow gradual ramping up of stimulation is provided over the course of a period of time greater than a period of one inspiration cycle, or over the course of time spanning multiple breaths, to gradually increase lung volume, provide a lung volume bias, and/or increase functional residual capacity. Stimulation may be ramped down as well. Among other things, the gradual ramping of stimulation may provide greater patient comfort, reduce a likelihood of arousal from stimulation, or may reduce sudden change in negative pressure as seen by to upper airway and thereby avoid upper airway closure during stimulation. Thus according to the invention stimulation provides a slow and/or gradual increase in lung volume. One or more stimulation parameters may be ramped including, e.g., pulse amplitude, frequency, pulse width, burst duration and/or burst frequency.

According to one aspect of the invention stimulation is alternated between hemidiaphragms to allow rest or prevent adaptation. Stimulation may be separately applied or otherwise controlled to each hemidiaphragm, by turning on or off stimulation or by changing stimulation parameters for one or both of the hemidiaphragms. The timing may also be separately controlled. Initialization, selection or application of stimulation parameters for each diaphragm may also be separate.

Similarly, stimulation may be alternated or rotated from one electrode or electrode pair (or group) to another in a multiple electrode assembly. Stimulation may be altered on the same hemidiaphragm or opposite hemidiaphragms.

Stimulation to each hemidiaphragm or each electrode (or electrode pair) may be ramped up and down separately or, for example one may be ramped up while the other is ramped down to provide a smoother transition and produce gradual changes in lung volume or other respiration parameters when switching stimulation from one hemidiaphragm to the other or from one electrode or electrode pair to another. Also one side may be stimulated first and then the other side to provide a more gradual increase in volume. Similarly a gradual ramp down may be provided by reducing stimulation to one hemidiaphragm and then the other.

In accordance with one aspect of the invention, stimulation is provided by varying one or more stimulation parameters, e.g., amplitudes, frequencies, pulse widths and/or burst durations or burst frequencies, to avoid fatigue or adaptation. Such stimulation parameters may be within a desired range or may be altered to provide an optimization of diaphragm rest and diaphragm activation. Such stimulation protocol may be generally open loop where a predetermined program or sequence is used for preset time periods to stimulate and also provide rest. Stimulation may be cycled through different amplitudes and/or frequencies or other parameters. Such stimulation protocol may also be generally closed loop where stimulation parameters are adjusted based on feedback indicating rest is needed or that adaptation is occurring. Stimulation may also be adjusted or cycled on or off depending upon a patient status, such as, for example, sleep state status, response to therapy, or other condition or status. Such protocol may be either open loop, closed loop or a combination thereof, e.g., wherein stimulation is provided for a period of time according to a protocol and then sensing is used to periodically determine stimulation and response status. For example, after a period of stimulation, detection or sensing may be used to determine if breathing is continuing to be stabilized after stimulation. Stabilized ventilation may be detected, for example, using methods and devices that determine variations in lung volume, tidal volume, functional residual capacity, flow, or other respiration parameter. Stimulation may be provided again when breathing stabilization has fallen off.

Stimulation may be individualized on a patient by patient basis by determining individual patient response to stimulation to result in an optimal or preferred functional residual lung volume or a sustained lung volume bias, to get a desired result. Detection as well as stimulation may be optimized or selected on a patient by patient basis where patient stability markers are determined e.g. using polysomnography data (for device initialization and/or device programming updating). Such initialization may provide a determination of functional residual capacity or change in functional residual capacity resulting from stimulation. Accordingly, a baseline functional residual capacity is sensed or observed as a reference point, stimulation is provided and response or change in FRC produced by the stimulation is sensed or observed. Functional residual capacity may be observed before, during and after stimulation. Such observation of stimulation and response may be while subject is awake or during sleep. A number of polysomnography markers may be used to determine effectiveness of stimulation such as: (volume changes, stability of flow, FRC, volume, arousals, arousals in response to or due to stimulation). To reduce arousals due to stimulation, stimulation parameters may be modified such as stimulation frequency, stimulation amplitude or stimulation ramping. Also stimulation to one or other hemidiphragm may be adjusted to provide a more gradual affect from stimulation. Other information may be used to determine adaptation to stimulation where the stimulation may be either more effective or less effective, or fatigue where the stimulation is less effective. Modification of stimulation parameters may be provided in response to such fatigue or adaptation. Such device initialization may be provided with external or temporary sensors, for example in a polysomnography study, or where appropriate when the patient is awake. Such device initialization may also be provided with sensors and/or detection incorporated into the stimulation device or its peripherals. Also such device initialization may be provided periodically or on an ongoing basis during the term of device usage. The device may be programmed to adjust stimulation parameters or protocol during the device usage term.

Such initialization may also be used to select a type of stimulation or stimulation protocol that is most effective for an individual's particular disorder, disease or breathing/disordered breathing. Such initialization may also be used to initialize detection Various detection algorithms may also be incorporated into the device to detect various conditions and/or trigger therapy. The device may be programmed to respond with adjustment, switching or turning on or off of stimulation based on various detections.

According to one aspect of the invention, an increase in FRC or a lung volume bias may be used for therapeutic purposes prior to materialization of an apnea event where breathing instability is present, even when no event is present or clearly imminent. According to one aspect, if then a central or obstructive apnea does occur, the device may either turn off stimulation, or provide stimulation according to a different protocol. Occurrence of an event or pattern of events may trigger stimulation to prevent future events.

Detection may comprise detecting flow limitations or unstable breathing that are not at an apnea level and turning on diaphragm stimulation to provide stability, improving gas exchange or ventilation to reduce flow limitation or stabilize breathing. For example obstructive apnea patients, unstable breathing or degree of flow limitation may be detected, or other indicators of a likelihood of obstruction occurring, for example other previous occurrence or pattern of occurrence of events. Stimulation may be accordingly be provided to increase functional residual capacity or provide a lung volume bias. If obstructive apnea occurs, stimulation may be turned off. Turning off stimulation may also be used to increase upper airway patency with increased exhalation or to increase airflow. Where a patient suffers from central apnea or mixed apneas, absent such event stimulation may be provided to increase functional residual capacity or provide a lung volume bias to regulate or manipulate gas exchange, improve ventilation and/or stabilize breathing to reduce conditions that lead to overshooting of respiratory drive as well as improving upper airway patency. If central apnea is detected then paced breathing may be provided until normal breathing resumes. After an arousal, a pattern of instability or flow limitations, or apnea event has occurred, stimulation may be turned on to prevent subsequent events. In accordance with this aspect of the invention, detection of apnea events, flow limitations or other respiratory disorders or instability may trigger turning on or off of therapy. Therapy may then be provided for a period of time or based on a detected respiratory state or otherwise controlled in a closed loop system.

According to one aspect of the invention, stimulated lung volume bias is a supplemental increase in lung volume that may be provided with intrinsic, paced or augmented breathing. It may also be provided with other breathing control scenarios.

According to another aspect of the invention, a first type of stimulation may be provided and subsequently switched to another type of stimulation. Such switch in stimulation type may be based on, for example, a determination of effectiveness or lack of effectiveness of the first type of stimulation or a change in condition.

According to one aspect of the invention a biased lung volume may be provided before, during and/or after other diaphragm stimulation among other things, to help avoid upper airway closure. Such other diaphragm stimulation or stimulation types may include for example, paced breathing, augmented breathing, deep inspiration stimulation, breathing control or manipulation of breathing, as well as high frequency contraction stimulation. According to another aspect of the invention a biased lung volume may be provided before other diaphragm stimulation among other things, to help avoid upper airway closure. According to another aspect of the invention a biased lung volume may be provided after other diaphragm stimulation among other things, to help avoid upper airway closure. According to another aspect of the invention a biased lung volume may be provided throughout other stimulation or a portion of other stimulation.

According to another aspect of the invention stimulation providing a biased lung volume may be turned off to increase upper airway patency where the sudden change in pleural pressure or outflow creates an opening of the upper airway prior to the next breath.

These and other aspects of the invention are set forth in the specification and claims herein.

BRIEF DESCRIPTION OF THE DRAWINGS

FIGS. 1A to 1C schematically illustrate lung volume, stimulation of the right hemidiaphragm and stimulation of the left hemidiaphragm respectively with a ramped up stimulation for creating lung volume bias and a ramped down stimulation.

FIGS. 2A to 2C schematically illustrate lung volume, a first stimulation signal at a first electrode and a second stimulation signal at a second electrode illustrating gradual ramping of stimulation and alternating stimulation at different locations.

FIGS. 3A to 3C schematically illustrate lung volume, a first stimulation signal at a first electrode and a second stimulation signal at a second electrode illustrating gradual ramping of stimulation and alternating stimulation at different locations.

FIGS. 8A to 8C schematically illustrate lung volume under different conditions and using different levels of bias stimulation.

FIGS. 10A to 10C schematically illustrate snoring (in decibels) tidal volume and stimulation respectively in accordance with an aspect of the invention.

DETAILED DESCRIPTION

Figure 4:
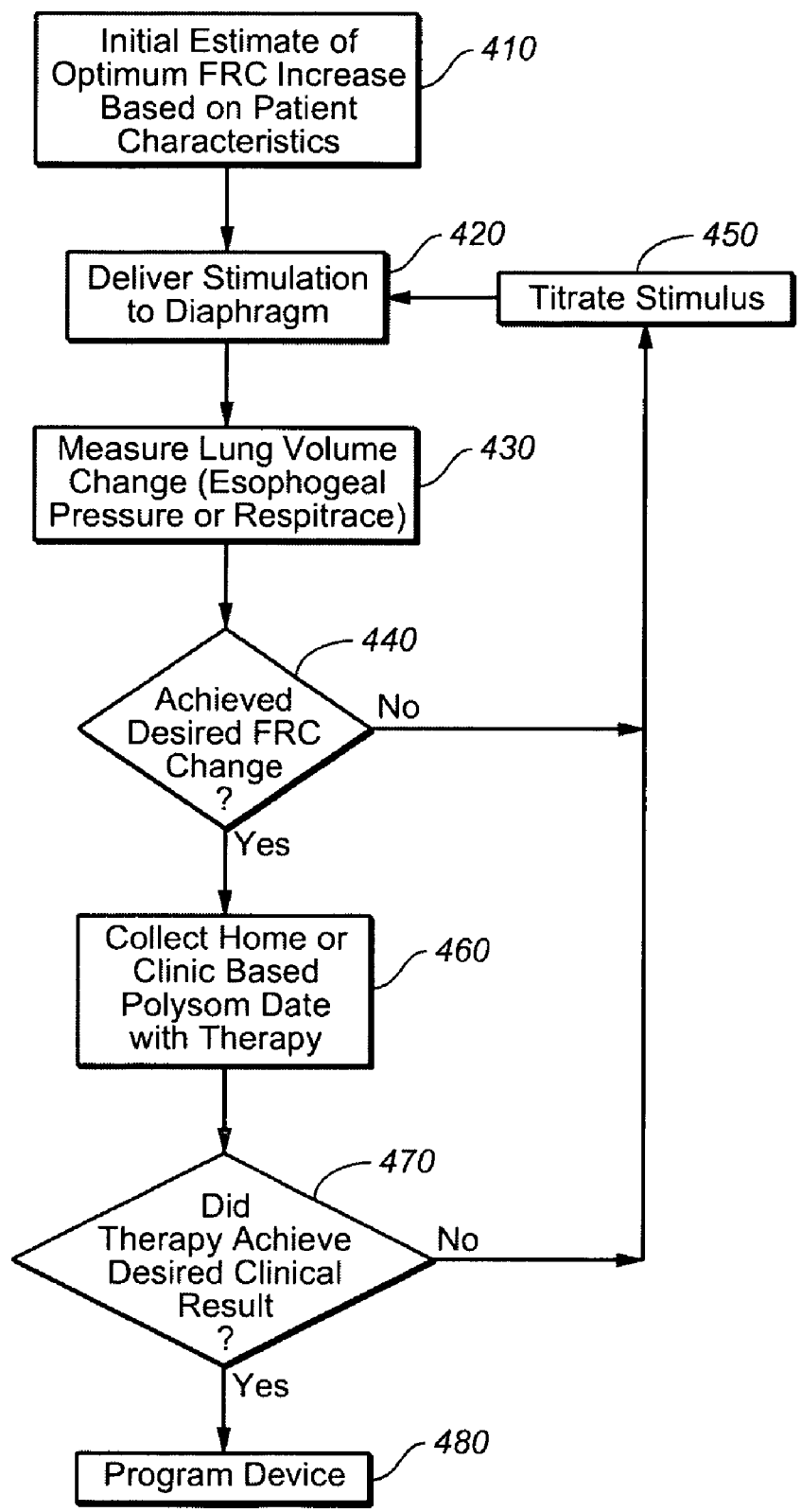
FIG. 4 is a flow diagram illustrating device initialization to achieve desired increase in FRC and/or sustained lung volume bias.

In accordance with one aspect of the invention slow gradual ramping up of stimulation is provided over the course of a period of time greater than a period of one inspiration cycle, or over the course of time spanning multiple breaths. For example, while not intending to be limited thereto, ramping may be provided over a period of about 5 to 60 seconds. The ramping up described may reduce arousals or waking from patient detection of stimulation. It is believed that among other things, ramping may improve patient comfort by producing more gradual diaphragm contraction and more gradual pressure changes. It is also believed that ramping may reduce the possibility of obstruction that may occur with a greater negative thoracic pressure.

Ramping describe herein may be titrated base on patient feedback such as sensation, or in a sleep lab.

FIGS. 1A to 1C illustrate a lung volume bias stimulation being ramped up and then down over a period of multiple breaths. The amplitude, frequency, pulse duration, burst duration, and/or burst frequency, may be modulated or ramped or slowly increased as schematically illustrated in FIGS. 1B and 1C. FIG. 1B illustrates a stimulation signal envelope 130 for stimulation of a right hemidiaphragm. The stimulation signal envelope 130 comprises a ramped portion 135 schematically illustrating the ramping up of the right hemidiaphragm signal over a plurality of breaths 121. FIG. 1B further illustrates a ramped portion 139 schematically illustrating ramping down of the right hemidiaphragm signal over a plurality of breaths 121. FIG. 1C illustrates a stimulation signal envelope 150 for stimulation of a left hemidiaphragm. The stimulation signal envelope 150 comprises a ramped portion 155 schematically illustrating the ramping up of the left hemidiaphragm signal over a plurality of breaths 121. FIG. 1C further illustrates a ramped portion 159 schematically illustrating ramping down of the left hemidiaphragm signal over a plurality of breaths 121. Stimulation to the right and left hemidiaphragms are generally synchronized as illustrated in FIGS. 1B and 1C. FIG. 1A illustrates a corresponding lung volume. Breaths 121 as illustrated in FIG. 1A are intrinsic breaths. However, ramping up and down of lung volume bias stimulation as illustrated in FIGS. 1B and 1C may also be used during paced breathing. A baseline lung volume 120 (initial functional residual capacity) is shown prior to stimulation. During the period of ramping stimulation 122, functional residual capacity is gradually increased from the baseline 120. Once the stimulation has been ramped, stimulation is leveled off for period 123. Stimulation is then ramped down for period 124 where functional residual capacity gradually decreases.

The gradual ramping periods 122 and 124 may be for a period greater than a normal intrinsic inspiration period or over a period spanning a plurality of breaths. While a lung volume bias is illustrated, other stimulation may be ramped up or down in accordance with an aspect of the invention.

In accordance with one aspect of the invention, a gradual increase in the duty cycle of bias situation may also be provided. The duty cycle may be independent of intrinsic respiration or may be synchronized with breathing.

In accordance with one aspect of the invention slow gradual ramping up of stimulation is provided with the stimulation offset between two hemidiaphragms or between two or more electrodes or electrode pairs. FIGS. 2A to 2C illustrate a lung volume bias stimulation being ramped up over a period of multiple breaths with ramping offset between hemidiaphragms. Stimulation may also be ramped down in an offset manner. The amplitude, frequency, pulse duration, burst duration, and/or burst frequency, may be modulated or ramped or slowly increased as schematically illustrated in FIGS. 2B and 2C. FIG. 2B illustrates a stimulation signal envelope 230 for stimulation of a right hemidiaphragm. The stimulation signal envelope 230 comprises a ramped portion 235 schematically illustrating the ramping up of the right hemidiaphragm signal for a period 222 over a plurality of breaths 221. FIG. 2C illustrates a stimulation signal envelope 250 for stimulation of a left hemidiaphragm. The stimulation signal envelope 250 comprises a ramped portion 255 schematically illustrating the ramping up of the left hemidiaphragm signal for a period 223 over a plurality of breaths 221. Stimulation to the right and left hemidiaphragms are offset as illustrated in FIGS. 2B and 2C. The periods 222 and 223 are offset from each other but overlap in time. Alternatively, the periods 222, 223 may be sequential. FIG. 2A illustrates a corresponding lung volume. Breaths 221 as illustrated in FIG. 2A are intrinsic breaths. However, ramping up and down of lung volume bias stimulation as illustrated in FIGS. 2B and 2C may also be used during paced breathing. A baseline lung volume 220 (initial functional residual capacity) is shown prior to stimulation. During the periods of ramping stimulation 222, 223 functional residual capacity is gradually increased from the baseline 220. Once the stimulation has been ramped, stimulation is leveled off at both hemi-diaphragms for a period of time.

The gradual ramping periods 222 and 223 may individually or in the aggregate be for a period greater than a normal intrinsic inspiration period or over a period during a plurality of breaths. While offset ramping is shown with respect to electrodes at two different hemidiaphragms, such offset ramping may be provided with any two or more electrodes or electrode pairs, whether positioned on the same hemidiaphragm or not. Offset ramping may be provided with more than two electrodes or electrode pairs where ramping occurs in the aggregate for a period greater than that of a normal intrinsic inspiration or for a period spanning multiple breaths.

The gradual ramping periods 222 and 223 may be for a period greater than a normal intrinsic inspiration period or over a period spanning a plurality of breaths. While a lung volume bias is illustrated, other stimulation may be ramped up or down in accordance with an aspect of the invention. Offset stimulation may also be used to prevent fatigue by resting stimulated portions of the diaphragm or phrenic nerve while maintaining stimulation on.

In accordance with one aspect of the invention switching of stimulation from one hemidiaphragm, electrode or electrode pair to another is provided. According to one aspect, stimulation is provided in a manner that maintains a therapeutic diaphragm contraction. FIGS. 3A to 3C illustrate a lung volume bias stimulation over a period of multiple breaths with ramping up of one hemidiaphragm and ramping down of the other hemidiaphragm. The amplitude, frequency, pulse duration, burst duration, and/or burst frequency, may be modulated or ramped or slowly increased as schematically illustrated in FIGS. 3B and 3C. FIG. 3B illustrates a stimulation signal envelope 330 for stimulation of a right hemidiaphragm. The stimulation signal envelope 330 comprises a ramped portion 335 schematically illustrating the ramping down of the right hemidiaphragm signal for a period 322 over a plurality of breaths 321. FIG. 3C illustrates a stimulation signal envelope 350 for stimulation of a left hemidiaphragm. The stimulation signal envelope 350 comprises a ramped portion 355 schematically illustrating the ramping up of the left hemidiaphragm signal for a period 323 over a plurality of breaths 321. The periods 322 and 323 overlap in time. FIG. 3A illustrates a corresponding lung volume. Breaths 321 as illustrated in FIG. 3A are intrinsic breaths. However, ramping up and down of lung volume bias stimulation as illustrated in FIGS. 3B and 3C may also be used during paced breathing. A baseline lung volume 320 (initial functional residual capacity) is shown prior to stimulation. During the periods of ramping respectively down and up of stimulation 322, 323, functional residual capacity is generally maintained above the baseline 320. The gradual ramping periods 222 and 223 may individually or in the aggregate be for a period greater than a normal intrinsic inspiration period or over a period during a plurality of breaths. While switched ramping is shown with respect to electrodes at two different hemidiaphragms, such switched ramping may be provided with any two or more electrodes or electrode pairs, whether positioned on the same hemidiaphragm or not. Switched ramping may be provided with more than two electrodes or electrode pairs providing overlapping stimulation with different electrodes or electrode pairs to permit rest of the diaphragm or nerve associated with an electrode or electrode pair.

The gradual ramping periods 322 and 323 may be for a period greater than a normal intrinsic inspiration period or over a period spanning a plurality of breaths. While a lung volume bias is illustrated, other stimulation may be ramped up or down in accordance with an aspect of the invention. This stimulation may be used to prevent fatigue by resting stimulated portions of the diaphragm or phrenic nerve while maintaining stimulation on.

In accordance with one aspect of the invention, stimulation is provided by varying one or more stimulation parameters, e.g., amplitudes, frequencies, pulse widths and/or burst durations or burst frequencies, stimulation on/off periods, to avoid fatigue or adaptation. Such stimulation parameters may be within a desired range or may be altered to provide an optimization of diaphragm rest and diaphragm activation. Such stimulation protocol may be generally open loop where a predetermined program or sequence is used for preset time periods to stimulate and also provide rest. Stimulation may be cycled through different amplitudes and/or frequencies. Such stimulation protocol may also be generally closed loop where stimulation parameters are adjusted based on feedback indicating rest is needed or that adaptation is occurring. Stimulation may also be adjusted or cycled on or off depending upon a patient status, such as, for example, sleep state status, or other condition or status. Such protocol may be a combination of open loop and closed loop wherein stimulation is provided for a period of time according to a protocol and then sensing is used to periodically determine stimulation and response status. For example, after a period of stimulation, detection or sensing may be used to determine if breathing is continuing to be stabilized after stimulation. Stabilized ventilation may be detected using methods and devices that determine variations in lung volume, tidal volume, functional residual capacity, flow, or other respiration parameter. Examples of detection are described in further detail herein or in related applications as set forth herein. Upon detection of stabilized ventilation, stimulation may be cycled off. Stimulation may be provided again when breathing stabilization has fallen off.

In accordance with one aspect of the invention, stimulation may be individualized on a patient by patient basis by determining individual patient response to stimulation, that will achieve a desired result. For example, polysomnography may be used to provide therapeutic and/or diagnostic data on individual patients by observing a patient's sleep data and by observing a patient's response to therapy. Specific types of therapy, combinations of therapy and/or therapy parameters may be titrated during polysomnography studies or during an initialization or reprogramming period after implant. Specific types of stimulation and/or combinations have been set forth herein and in related applications as set forth herein. A number of polysomnography markers may be used to determine effectiveness of stimulation or combinations of stimulation such as: volume changes, stability of flow, removal of flow limitation, FRC, volume, arousals, arousals in response to or due to stimulation, AHI, SaO2 levels. Polysomnography may be used for decisions or initialization for bias therapy, therapy where FRC is increased, or for using other therapies such as paced breathing, breathing control, augmented breathing, deep inspiration, duty cycle manipulation or others for exampled as described in co-pending applications set for the herein.

In accordance with an aspect of the invention, initialization, for example, may provide a determination of a desired therapeutic functional residual capacity or change in functional residual capacity to be achieved from stimulation. According to an aspect normal lung volume levels may be determined such as a normal or non-pathological tidal volume and functional residual capacities may be determined. Lung volumes may then be observed prior to respiratory disordered events for example prior to flow limitations, arousals or apneas occurring. Therapeutic stimulation may be provided to raise lung volume to a non-pathological or normal level. Based on initialization data, lung volume bias therapy or other therapy such as breathing augmentation or other therapy to maintain minute ventilation above the critical level may be provided when the critical threshold has been reached. Minute ventilation may be calculated on a breath by breath basis, as a running average or over a predetermined period of time. Thus drops in tidal volume, FRC or minute ventilation may trigger therapy where no apnea is present.

In accordance with another aspect of the invention, ranges of normal and/or out of range parameters may be set based on initialized data acquisition and analysis.

In accordance with one aspect of the invention, the change in lung volume from awake to sleep may be observed and set as a therapeutic lung volume.

According to one aspect, using polysomnography data, a calculation may be made as to when or at what minute ventilation the patient's SaO2 levels drop below a critical level. Such critical level may be defined as a level sufficiently before apnea occurs (Alternatively it may be defined as a level approximately when apneas occur).

Also, a maximum lung volume or minute ventilation may be set for example, where therapy may be turned off. Such maximum level may be set, for example as a normal lung volume level plus a percentage of normal lung volume (e.g., tidal volume or FRC). Alternatively a maximum minute ventilation may be determined and set as a normal level plus a percentage of such level. Minimum and maximum $SaO_2$ levels may also be set. $SaO_2$ may be observed in sleep studies and corresponding to other parameters such as minute ventilation, lung volume and/or FRC. Or during treatment, such levels may be detected. Thus if with stimulation tidal volume, minute ventilation, $SaO_2$ or other physiological parameter exceeds a desired or safe level, stimulation may be turned off or adjusted. Also if a normal level of breathing resumes on top of stimulation, such lung volume or minute ventilation levels may exceed a desired level and stimulation may be turned off or the patient weaned off of stimulation. In accordance with one aspect of the invention a clinical protocol may be defined where different FRC increases are tested until a satisfactory improvement in disease state is obtained. Such as reduced respiratory disturbances or events, improved $SaO_2$ levels, improved breathing or improved cardiovascular function.

According to another aspect an external programming device may be provided with software that calculates a recommended therapeutic volume increase based on patient's weight, sex abdominal and neck diameter and AHI. This may be used as an initial value which may then be further titrated.

Detection as well as therapy parameters may be individualized on a patient by patient basis where patient stability markers are determined e.g. using polysomnography data (for device initialization and/or device programming updating). Stability markers may include parameters or combination of parameters that are used to create detection criteria for unstable breathing. For example, polysomnography data may be recorded for a period of time where normal breathing is occurring. Ranges of normal variations in respiratory parameters may be defined. A statistical analysis may be used to determine or define a range of normal parameters or combinations of parameters. Also, the changes that occur with the onset of disordered breathing can be quantified and used to initialize detection criteria, thresholds or ranges.

Referring to FIG. 4, a flow diagram illustrates an example of individualizing stimulation to provide a desired functional residual capacity or biased lung volume. An initial estimate of an optimum FRC increase is determined based on patient characteristics 410. Such characteristics for example, may be height, sex, BMI, breathing pattern (such as a breathing pattern prior to or leading to an obstruction or other disordered event) or AHI as determined from sleep study. Another characteristic or pattern that might be observed is a percent of hypopnea events versus apnea. This information may be used to tailor treatment, for example by setting FRC target higher where there are greater numbers of apneas and lower where there are fewer. Stimulation is then provided to the diaphragm or phrenic nerve 420 using the therapeutic device. Lung volume change is then sensed, observed or determined including change in functional residual capacity 430 either in synchrony with stimulation or lasting for a period after stimulation. For example, the change in FRC produced by stimulus may be observed using a belt with sensors that measure the displacement of the chest and abdomen. A magnetometer may be used to measure chest wall displacement, which is correlated with lung volume, or a measurement of esophageal pressure may be used in order to determine a change in intrapleural pressure indicative of a lung volume change. Then it is determined whether the lung volume change is at a desired level or not 440. If it is not, then the stimulation is adjusted or titrated 450. This titration (or stimulation with the device) may also be done for the left and right hemidiaphragms individually or together in order to achieve the desired volume change. In addition, stimulation during initialization or device use that is provided may be unilateral using either right or left diaphragm alone. If the desired FRC is achieved, then the patient is observed in sleep in a clinic at home collecting sensed data including that typically observed during polysomnography studies 460 using the titrated parameters. Information may be telecommunicated as well. Then it is determined whether the therapy achieved a desired clinical result with the initialized stimulation parameters using the polysomnography data or sensed data 470. Typically such observations may be air flow, EEG, abdominal and rib movement, snore sensor, and SaO2 that determine the occurrence of apnea or hypopnea events (e.g. apnea/hypopnea index (AHI)), breathing stability, arousals, oxygen saturation, presence of snoring or any other data that indicates effectiveness of therapy. A polysomnography study may show criteria such as improvement in AHI, arousal index and SaO2 saturation levels. Additionally or alternatively, a sleep study without applied therapy may be used as a control to determine if the stimulation using particular parameters or protocols resulted in an improvement in any of the clinical parameters observed on the polysomnograph. If the therapy did not achieve the clinical result, the stimulus is titrated. The titration may be done incrementally during one or more studies, or it may be adjusted based on information accumulated from the previous titration. For example, earlier titrations may provide information concerning the dose response, or stimulation parameters associated with corresponding volume change. If the therapy did achieve the desired clinical result, then the stimulation parameters are set or programmed into the therapeutic device 480 until the device is reprogrammed. In accordance with one aspect of this example, minute ventilation or other respiratory parameters may be observed and used in addition or as an alternative to using lung volume, for example in step 430.

During a sleep study prior to device implant, data may be collected that includes a diaphragm EMG signal. The signal may be recorded and analyzed during different respiratory states such as flow limitation, obstruction, reduced central drive, and central apnea. This analysis may be used to set EMG based thresholds for detection of these conditions or events. For example, the EMG envelope may be calculated, and the width of the envelope may be determined for each of these conditions. Using statistical methods, thresholds may be determined based on EMG envelope width that differentiate, for example, flow limitation from obstruction, or normal breathing from reduced central drive. A diaphragm EMG may be used to correlate changes in EMG to a specific respiratory disorder, disturbance or disease on the EMG.

To reduce arousals due to stimulation, stimulation parameters may be modified such as stimulation frequency, stimulation amplitude or stimulation ramping. This may be implemented, for example at or prior to device implant. Also stimulation to one or other hemidiaphragm may be adjusted.

Other information may be used to determine adaptation to stimulation where the stimulation may be more effective or less effective, or fatigue where the stimulation is less effective. Modification of stimulation parameters may provided in response to such fatigue or adaptation. Such adjustment of parameters may be provided by monitoring patient response over time or in a device with continuous or periodic feedback and adjustment of parameters based on response to stimulation.

Device initialization may be provided with input from external or temporary sensors, for example in a polysomnography study, or where appropriate when the patient is awake. Such device initialization may also be provided with sensors and/or detection incorporated into the stimulation device or its peripherals. Also such device initialization may be provided periodically or on an ongoing basis during the term of device usage. The device may be programmed to adjust stimulation parameters or protocol during the device usage term.

In addition to sensing EMG, for initialization or detection, ECG may be sensed, e.g., from the implanted device, and the data used to initialize the device or provide feedback during device use. Heart rate variability, Heart rate RR intervals, may be sensed with sleep data gathered for a night and analyzed for device initialization or programming or reprogramming.

An implantable device may match its sleep disordered breathing detection with an automated sleep scoring system (for example Morpheus of SleepMed inc. has such an automated scoring system) may be used to calibrate implant as well.

Various detection algorithms may also be incorporated into the device. The device may be programmed to respond with adjustment of parameters or turning on or off of stimulation based on various detections. Detection and detection thresholds may be based on data polysomnography or data gathered in a real time therapy device According to one aspect of the invention, an increase in FRC or a lung volume bias may be used for therapeutic purposes prior to materialization of an apnea event where breathing instability is present. Accordingly detection may comprises detecting flow limitations or unstable breathing that are not at an apnea level and providing stability, improving gas exchange or ventilation to avoid apnea. The device may also detect an imminent apnea event or onset of an apnea event. If a central or obstructive apnea does occur, the device may either turn off stimulation, or provide stimulation according to a different protocol. The device may also detect an apnea event or events that may indicate possibility of subsequent events occurring and may turn on stimulation after an apnea event has resolved.

Table I is a chart illustrating examples of conditions that may be detected to trigger a therapy. Detection of one or more conditions may indicate a respiratory disturbance and/or an imminent disordered event occurring. It is believed in accordance with the invention that a variety of diseases, disorder or conditions can be treated or prevented using one or more stimulation therapies including those described herein and in related applications as set forth herein. It is also believed that therapies that stabilize breathing, assist in maintaining respiratory drive at a desired level and/or reducing flow limitations helps reduce arousals prevent onset of respiratory events such as Cheyne Stokes Respiration or one or more types of apnea.

According to one aspect, one or more respiratory disturbances or indicators is detected and a first treatment is provided in response. Onset of a disordered breathing event such as an apnea may be detected, then a second treatment protocol may be implemented or the first treatment may be modified. Alternatively, occurrence of a disordered breathing event such as an apnea may be detected then a second treatment protocol may be implemented or the first treatment may be modified.

While not intending to be limiting, Table I provides an examples of indicators that may be detected. These indicators may be detected, for example, by sensing one or more respiration parameters as described herein or in one or more related patent applications as set forth herein.

| Conditions to Detect Conditions that Indicate Respiratory Disturbance | Possible Indicators of Condition |
|---|---|
| Instability of Breathing | Greater than normal variation of breathing rate, TV, or FRC |
| Reduction in Central Drive | Reduced diaphragm EMG (i.e. area under the "envelope") |
| Flow Limitation | Increased amplitude, width and frequency content of diaphragm EMG; change, e.g., flattening of morphology |
| Previous Central or Obstructive Apnea Events | Recent events: EMG below threshold for breath detection, amplitude, width and frequency content of diaphragm EMG over threshold for obstructive apnea |
| Imminent Disordered Event | Sleep data to identify indicators of imminent disordered event including respiratory parameters, blood gas levels or other physiological parameters identified from sleep data observation |
| Airway obstruction (or Disordered Event Onset) | Further increase amplitude, width and frequency content of diaphragm EMG, over that of flow limitation |
| Central apnea (or Disordered Event Onset) | EMG amplitude that is below threshold for breath detection. |

Detecting unstable breathing and providing stimulation such as, for example, bias, augmentation, paced breathing or breathing control may treat one or more diseases, disorders of conditions associated with unstable breathing and may prevent disordered breathing events. Unstable breathing may be detected by sensing a greater than normal variation in one or more respiratory parameters. It also may be detected for example by sensing snoring, for example as described in more detail herein. Patterns of breathing instability may be observed. For example if breathing instability occurs through out the night or increases, then stimulation may be provided or tailored to that pattern to reduce the occurrence of unstable breathing or related events.

Detecting a reduction in central drive and providing stimulation such as bias may prevent an obstructive event that can occur during or following a reduction in central drive. Also augmenting breathing or pacing breathing may be used to treat a reduction in central drive. Reduction in central drive may be detected by observing drops in tidal volume or slope of tidal volume waveform or one or more parameters of the EMG complex. In accordance with one aspect an average tidal volume over a period of time may be calculated. A threshold may be determined based on that average below which a drop in tidal volume or a drop in flow is detected. The tidal volume or current flow will be compared to that threshold. If it is less than the threshold, then a reduction in central drive is detected. Detection occurs when a drop in tidal volume or flow occurs. This allows the start of stimulation before onset of an obstructive episode or central episode.

Detecting a flow limitation and providing stimulation such as described herein may be used to reduce flow limitations and possible sleep disordered events. A flow or EMG template may be recorded during flow limitation at initialization. Then during device operation the current flow or one or more parameters of an EMG waveform may be compared to the template. If there is a close enough match to the template then a flow limitation is detected. Additionally, flow limitation may worsen over time. A threshold may be set based on the degree of limitation and number of flow limitation episodes that are observed.

Detection of the occurrence of a previous disordered events may be used to trigger therapy or to prevent subsequent events. For example after an event or pattern of events have occurred, stimulation may be turned on to increase functional residual capacity to reduce the likelihood of further events occurring. Other stimulation may also be triggered as well, by detecting events that have occurred. There may be a threshold set such that a certain number of events must occur before therapy is delivered.

Detecting the imminent onset of a disordered event may trigger therapy such as bias therapy to prevent the event from occurring. Bias therapy may reduce instability, improve gas exchange while permitting intrinsic breathing to continue. Sleep data to identify indicators of imminent disordered event may include changes in respiratory parameters such as in flow, tidal volume, FRC, blood gas levels, certain slope of drop in tidal volume, or other physiological parameter changes that occur immediately prior to an obstructive event. Patterns of change or values of such parameters, identified from sleep data observation may be stored as data. Then parameters from one or more breaths may be observed and analyzed, searching for a repetition of the pattern.

A further increase in amplitude, width and/or frequency content of diaphragm EMG, over that of flow limitation may be used to detect an obstructive event. Recordings of a known EMG during obstruction may also be used as a template for comparison to a current template to detect and obstructive event. For example, if more than a certain number of parameters of the template similar within a given percent margin, then OSA will be detected.

If an EMG amplitude is below a threshold for breath detection, a central event may be detected. Stimulation may be turned off to prevent obstructions, or paced breathing may be provided.

Figure 5A:
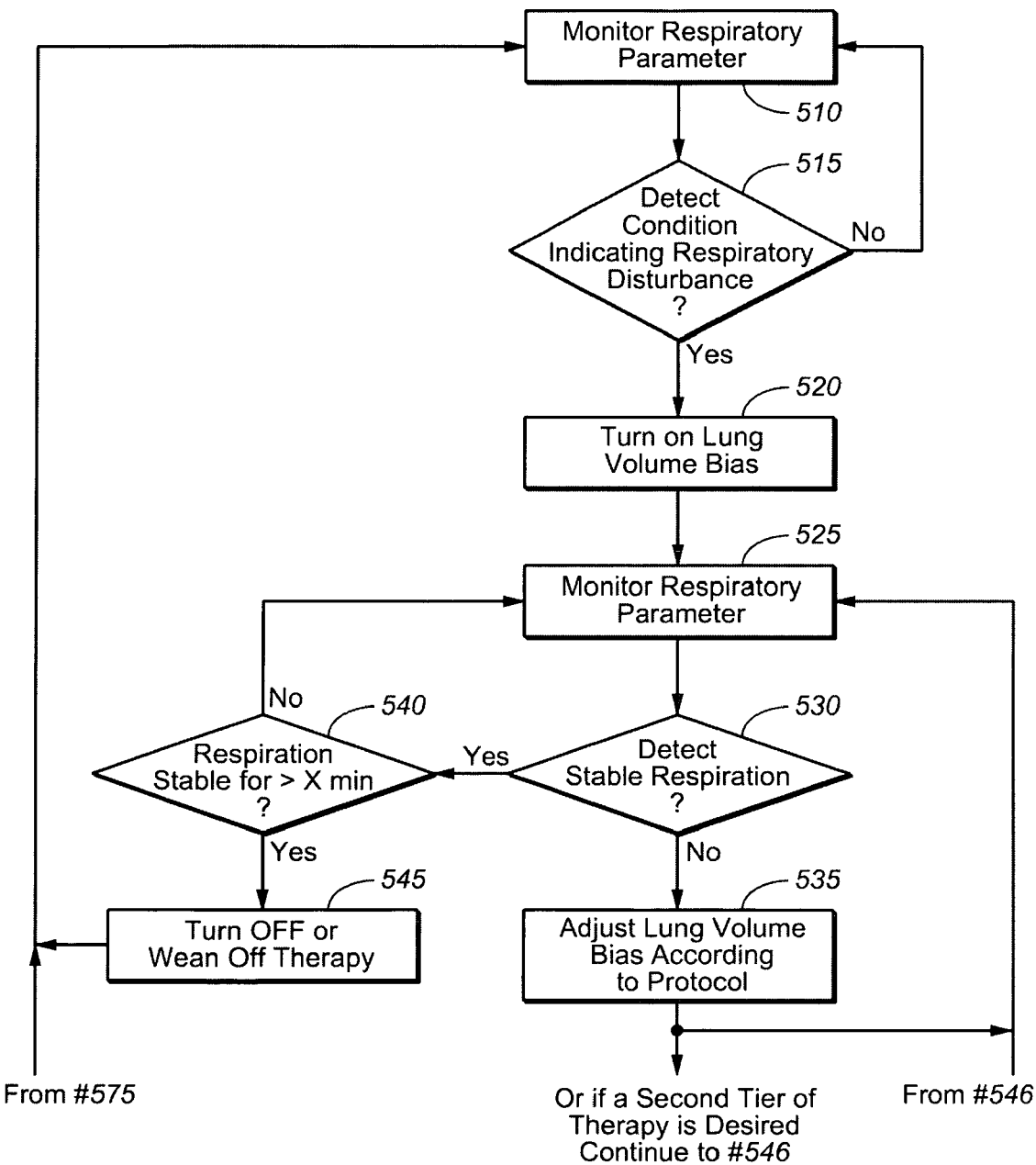
FIGS. 5A to 5C are flow diagrams illustrating detection and therapy in accordance with the invention.

FIG. 5A is a flow chart illustrating detection and treatment using a device or method in accordance with one aspect of the invention. One or more respiration parameters are monitored 510. One or more conditions are detected indicating a respiratory disturbance 515. Therapy is turned on to increase FRC or to create a lung volume bias 520. One or more respiration parameters are then monitored 525 to determine if respiration is stable 530. If respiration is not stable, the lung volume bias or therapy to increase FRC is adjusted according to a protocol 535. If respiration is stable then after respiration has been stable for a predetermined period of time 540, therapy is turned off of the patient is weaned off of therapy 545. If respiration is not stable for the predetermined period of time 540 then the respiration parameter is monitored again to detect stable respiration 525 and 530.

Figure 5B:
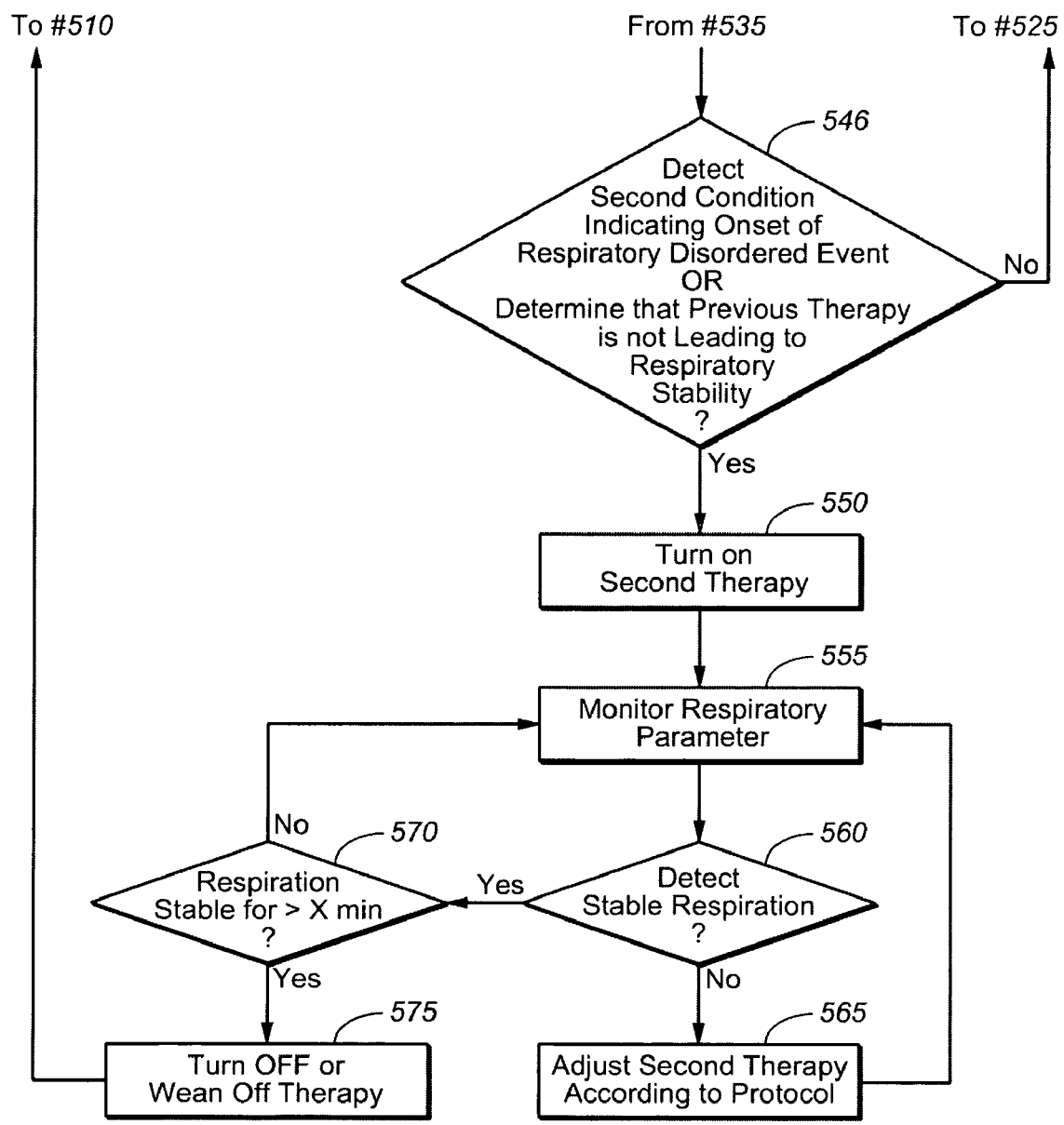

In accordance with another aspect of the invention as illustrated in FIG. 5B, a second detection may be added to the detection and treatment of FIG. 5A. If the second detection is added, then at step 535 if respiration is not stable and if a second condition is detected indicating an onset or an imminent or present respiratory disordered event or if a determination is made that previous therapy is not leading to respiratory stability 546, then therapy is adjusted or a second therapy is provided 550. One example of such adjustment may be, for example, if flow limitation still is detected after bias stimulation, stimulation may be switched to a stimulation protocol to increase inspiration duration.

One or more respiratory parameters are monitored 555. If respiration has not stabilized 560 then therapy is adjusted according to a protocol 565 and respiration is monitored again at step 555. If respiration is stable then if respiration has been stable for a preset period of time 570 therapy is turned off of the patient is weaned from the therapy 575 respiration is then monitored again at step 510 (FIG. 5A). If respiration has not been stable for a preset period of time 570 then therapy is returned to step 555. An example of a second therapy may be paced breathing if a central apnea is detected or a turn off of therapy if an obstruction is detected. The step of detecting if a second condition is present may also determine such second condition from one or more types of conditions. For example detecting the second condition may detect obstructive apnea or central apnea and determine which type of apnea is occurring or has occurred. If at step 546 a second condition is not detected indicating an onset or an imminent or present respiratory disordered event and if a determination is not made that previous therapy is not leading to respiratory stability, then return to step 525

Figure 5C:
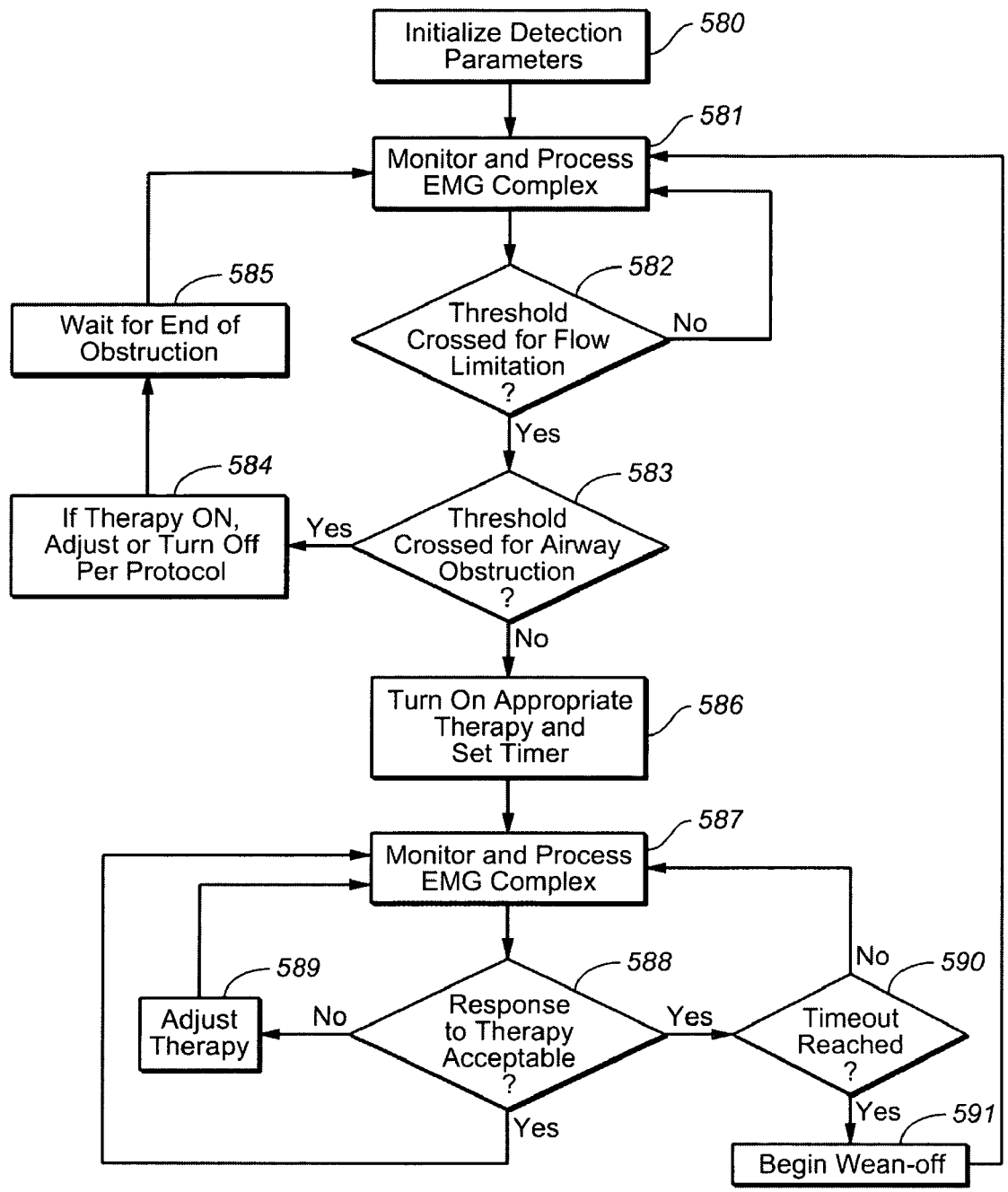

FIG. 5C is a flow chart illustrating detection and treatment for upper airway flow limitation or obstruction. Detection parameters are initialized 580, e.g., in a manner as set forth herein. The EMG complex is processed and monitored 581 to determine if a flow limitation threshold has been crossed 582, for example, as described in more detail with respect to FIGS. 6A-6E herein. If the threshold for flow limitation has not been crossed then monitoring continues at step 581. If the threshold for flow limitation has been crossed 582, then it is determined whether the flow limitation has also crossed the threshold for airway obstruction 583. If there is an airway obstruction, then the therapy is turned on, turned off or adjusted according to a protocol where appropriate 584 until the end of the obstruction 585 after which monitoring resumes at step 581. If at step 583, a threshold has not been crossed for airway obstruction then the appropriate therapy is turned on and a timer is set 586. The EMG complex is then monitored and processed 587. It is then determined if the response to the therapy is acceptable 588. If it is not, then therapy is adjusted 589 and monitoring continues at step 587. If the response to the therapy is acceptable at step 588, then if a timeout (preset time period) has not been reached 590 monitoring continues at step 587. If the response to the therapy is acceptable at step 588 and a timeout has been reached at step 590, then the patient is weaned off of the therapy 591 and monitoring begins again at step 581.

In addition to using detection of respiratory instability, respiratory disorders or imminent onset of a respiratory disorder to trigger therapy, therapy may be triggered after an event (or a number of events) has occurred such as an obstructive or central event. According to an embodiment, detection of an arousal may trigger delayed turning on of bias stimulation. Bias stimulation may then be turned on for a period of time. An occurrence of an event or events may indicate that a patient is more susceptible to additional events occurring and a therapy such as a bias therapy may be turned on for a predetermined period of time. A number of physiological conditions may increase likelihood of events such as onset of sleep or a particular sleep state. Detection of such events may also be used to trigger therapy where the events are known to increase a patient's susceptibility to apneas or other respiratory disorders.

A patient's episode patterns may be observed and therapy type or combinations of therapies may be selected. During polysomnography study for device initialization, a number of different therapies or combination may be evaluated or titrated based on observed patterns before or resulting from tested or trial therapy. If, for example, there is a tendency for central or mixed apneas, detection or therapy may be keyed to specific patient pattern. A type of therapy for a particular pattern may be selected, for example if the event is primarily central, a particular therapy may be selected; if the event starts as an obstructive event and then continues as a central event another therapy may be selected. For example, if a patient has a tendency to have events that are obstructive or flow limited followed by mixed events, bias therapy may be turned on at an early indication of breathing instability, to stabilize breathing by improving stability of the upper airway or of flow. In a patient with disordered breathing that tends to be initially centrally mediated, bias may be turned on prior to an event, followed by stimulation during breathing to augment breathing or paced breathing to treat the centrally mediated disorder.

In a closed loop system, it may be desirable to avoid turning on during periods of severe flow limitation as stimulation during such periods may not be as efficient particularly where severe airway resistance reduces the ability of stimulation to increase functional residual capacity. Timing of bias may be synchronized with respiration so that it provides a more efficient increase in functional residual capacity (as the airway is already opening and breathing is occurring).

In addition to detection set forth above, as a safety mechanism, the device may be provided with sensors that confirm that breathing is occurring on top of bias stimulation In accordance with another aspect of the invention, sensing may be provided of external or environmental conditions for example atmospheric pressure changes due to change in altitude. Stimulation or detection may be adjusted base on such external or environmental characteristics.

In accordance with one aspect of the invention, a plurality of thresholds are used to determine a plurality of levels of airway obstruction or flow limitation.

Detection of thresholds for flow limitation and complete obstruction in accordance with the invention may be determined related to the effort or magnitude of effort. As effort increases, a number of features in the EMG complex change. EMG envelope has been used to determine effort. The EMG envelop is obtained using an averaging process. However the EMG envelope determination process does not take into account all of the different magnitude changes that occur in an EMG complex with an increase in effort. Such factors include the frequency content changes, the width of the complex increase, increase in rising slope of EMG envelope and the increase in amplitudes and density of the individual spikes. In accordance with one aspect of the invention, an improved detection of effort is provided which takes into account one or more of the factors of the EMG complex. In accordance with another aspect of the invention in order to obtain a more accurate determination of effort, a plurality of factors of the EMG complex are used to determine degree of obstruction or flow limitation. For example, a power spectral density plot of EMG may be used to determine effort. Also frequency content of an EMG may be used to determine effort. Because frequency content increases with increased effort, the area under the Power Spectral Density Plot, e.g., between 100 and 500 Hz increases for flow limited activation (breath) versus non flow limited activation. A threshold may be set corresponding to an area under the PSD for detecting flow limitation or obstruction.

Figure 6A:
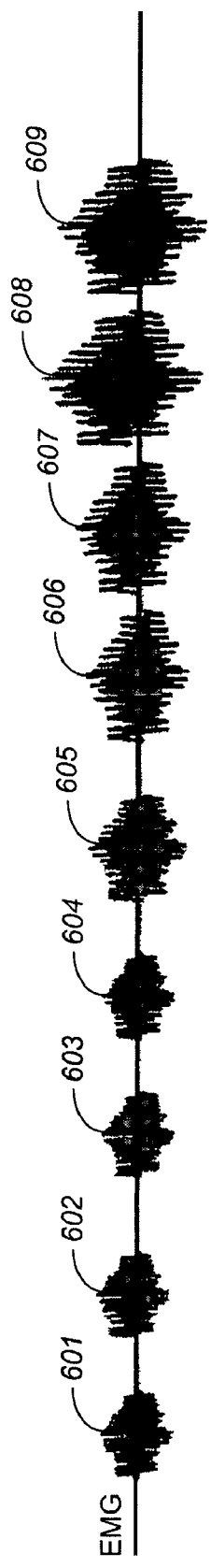
FIGS. 6A to 6C respectively schematically illustrate EMG, EMG envelope and tidal volume of a subject over varying degrees of airway patency.
Figure 6B:
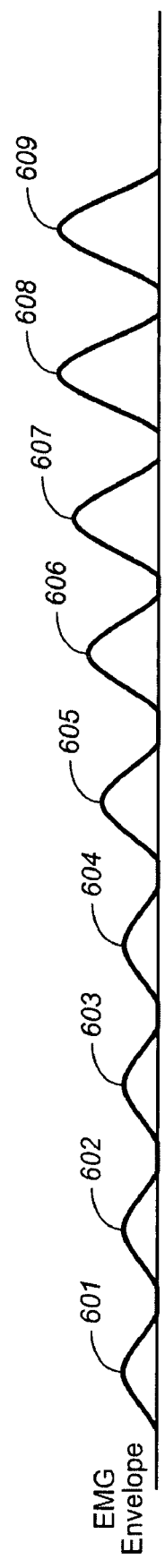
Figure 6C:
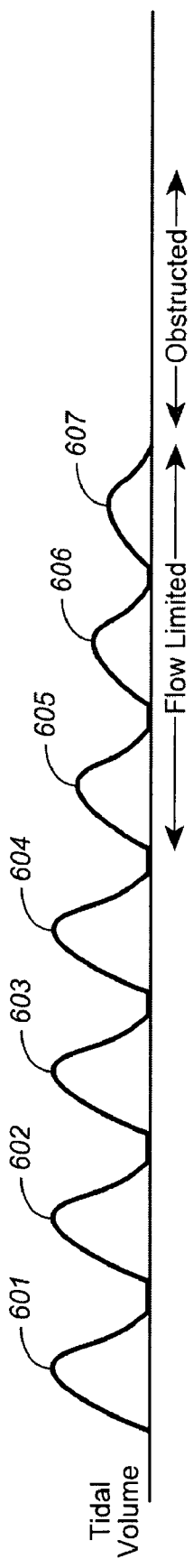

Referring to FIGS. 6A, 6B and 6C, EMG, EMG envelope and tidal volume are illustrated under different levels of flow limitation. The diaphragm EMG as well as upper airway (genioglossal EMG and intercostals show an increased activity with increased breathing effort. The increased activity can be measured through processing of the diaphragm EMG or EMG from other respiratory muscles to obtain an EMG envelope for each phasic activity. The envelope can be created by rectifying the signal, performing a window average over about 100 ms performing peak detection to obtain an envelope amplitude, and an integration of the area under the averaged signal to produce an envelope area. This processing to obtain an EMG envelope is generally known in the art. In accordance with one aspect, the phase of the diaphragm EMG with respect to other respiratory muscles may indicate obstruction or flow limitation. In accordance with one aspect of the invention, the EMG envelop may be used to differentiate between flow limitation and a greater level of obstruction. Where there is a flow limitation or flow obstruction, effort increases as does the EMG envelope amplitude. In addition as effort increases, e.g. due to greater limited flow or increased flow resistance, a number of features in the EMG complex change. The frequency content increases, the amplitude of the EMG spikes increases, the rising slope of the EMG complex increases and the width of the complex increases and the area under the envelope increases. One or more of the parameters may be used to identify when there is a flow limitation or when there is a flow obstruction. One or more thresholds may be set to determine one or more of these conditions.

Breaths 601, 602, 603, 604 show a normal EMG with a normal EMG envelope and a normal tidal volume. Breath 605 shows an increased EMG envelope (FIG. 6B), a reduced tidal volume and an EMG complex (FIG. 6A) with higher amplitude and components of increased frequency, indicating a flow limitation. Breaths 606, 607, 608 and 609 show a further increased EMG envelope (FIG. 6B), a further reduced tidal volume and a EMG complex (FIG. 6A) with even higher amplitude and components of increased frequency, indicating a flow obstruction. As shown in FIG. 6E the EMG envelope for a flow limited breath is greater in amplitude and duration for a flow limited breath 650 as compared to those of a normal breath 640. The EMG envelope for a flow obstructed breath 660 is greater in amplitude and duration than the EMG for a lower level flow limited breath 650. Thus using an EMG envelope, the increase in the envelope can be sensed or determined and used to determine when a flow limitation is occurring at a first threshold, and where an obstruction is occurring at a second threshold. The thresholds may be determined on a patient by patient basis. The thresholds may also distinguish degrees of flow limitation as well as flow limitation being distinguished from an obstruction, or either being distinguished form a normal breath.

Figure 6D:
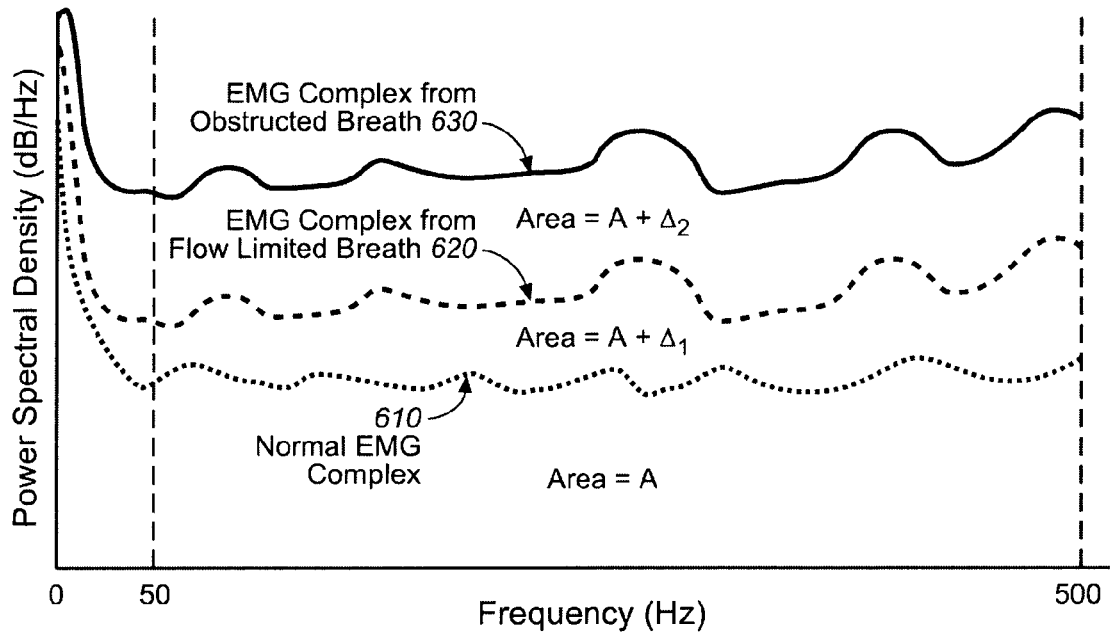
FIG. 6D is a power spectral density diagram for three EMG signals corresponding to varying degrees of airway patency.
Figure 6E:
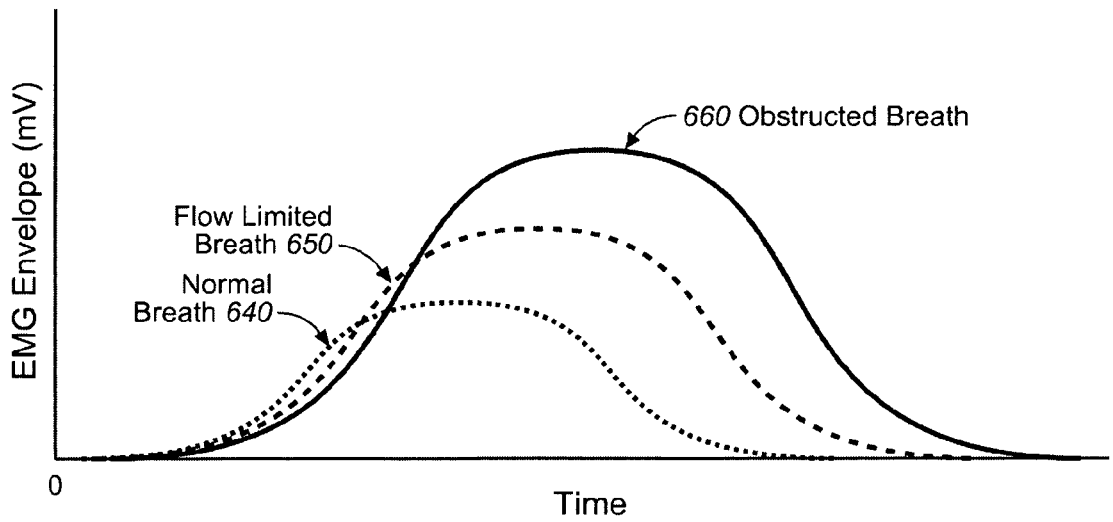
FIG. 6E is a schematic diagram of EMG envelope under different conditions.

As shown in FIG. 6D a Power Spectral Density (PSD) plot is illustrated of an EMG complex of a normal breath 610, of an EMG complex of a flow limited breath 620 and an EMG complex of an obstructed breath 630. As can be seen, there is an increase power density of higher frequency components of the EMG as obstruction occurs to a greater degree. The area under the PSD curve within a particular frequency range may be used to determine normal breathing versus flow limited breathing versus upper airway obstruction. Because the frequency content increases with increased effort, the area under the Power Spectral Density Plot between 100 Hz and 500 Hz (or the PSD in that bandwidth) increases as flow limitation increases. Thus using an EMG signal, the increase in frequency content of the complexes can be sensed or determined and used to determine when a flow limitation is occurring at a first threshold, and where an obstruction is occurring at a second threshold. The thresholds may be determined on a patient by patient basis. The thresholds may also distinguish degrees of flow limitation as well as flow limitation being distinguished from an obstruction or either being distinguished form a normal breath.

Figure 7A:
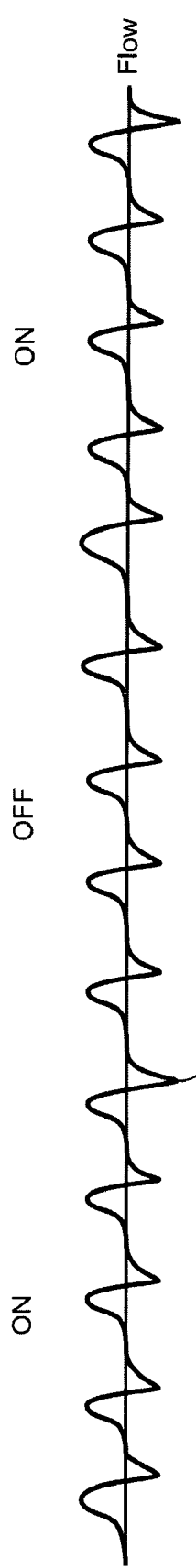
FIGS. 7A to 7C schematically illustrate flow, lung volume and stimulation respectively in accordance with one aspect of the invention.
Figure 7B:
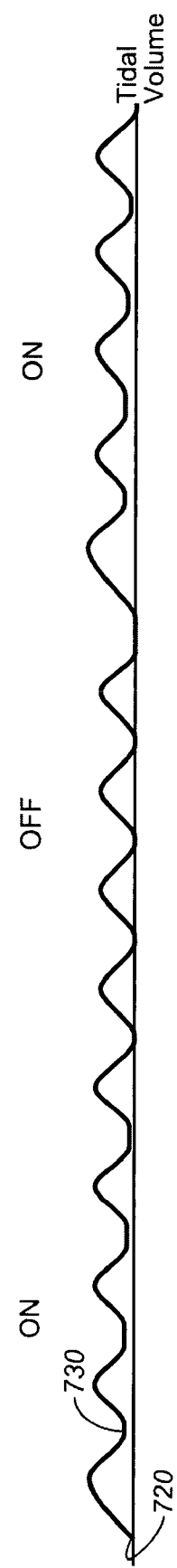
Figure 7C:
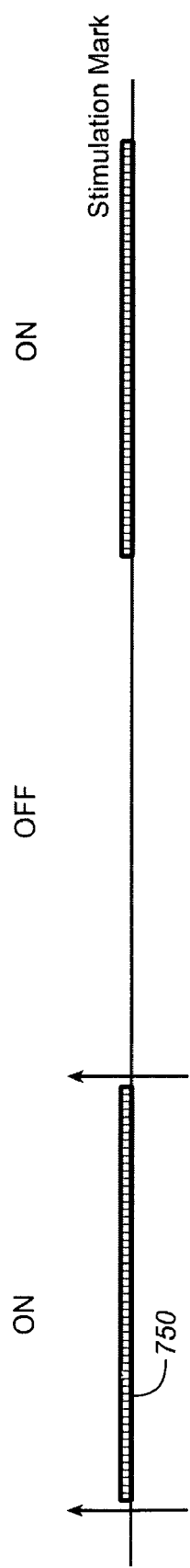

FIGS. 7A-7C illustrate use of a device and method whereby a bias stimulation is provided for a period over more than one breath and preferably several breaths.

According to another aspect of the invention, the stimulation is cycled off (or on) at a preselected portion of a respiration cycle. FIGS. 7A-7C further illustrate use of a device and method whereby a bias stimulation is provided and then is turned off to create a therapeutic benefit. Bias stimulation 750 (FIG. 7C) is provided to thereby increase functional residual capacity from a baseline 720 to an increased biased level 730 (FIG. 7B). Stimulation is turned off at the end of inspiration or the beginning of exhalation which provides an increased negative flow 710 (FIG. 7A), and increased positive pressure in the upper airway during exhalation. In accordance with one aspect of the invention, bias is cycled off to provide an increase in upper airway patency.

FIGS. 8A-8C illustrate different levels of increased FRC (e.g. from a reference point) achieved by different levels of low level bias stimulation. As can be seen low level bias stimulation can increase FRC in different amounts to achieve a desired therapeutic effect. In FIG. 8A a baseline FRC 810 is at about 3 Liters of volume above a residual lung volume 805. Stimulation is turned on at point 815. Stimulation is provided where functional residual capacity 820 is increased to about 3.5 liters, e.g., the FRC change is below the tidal volume 822 of a normal intrinsic breath 821. The FRC is increased by about 0.5 liter or ½ of a tidal volume of about 1 liter. In FIG. 8B a baseline FRC 830 is at about 3 Liters of volume above a residual lung volume 825. Stimulation is turned on at point 835. Stimulation is provided where functional residual capacity 840 is increased to about 4 liters, e.g., approximately at the tidal volume 842 of a normal intrinsic breath 841. The FRC is increased by about 1 liter or about the same as tidal volume of about 1 liter. In FIG. 8C a baseline FRC 850 is at about 3 Liters of volume above a residual lung volume 845. Stimulation is turned on at point 855. Stimulation is provided where functional residual capacity 860 is increased to about 4.5 liters, e.g., the FRC increase is above the tidal volume 862 of a normal intrinsic breath 861. The FRC is increased by about 1.5 liter or 1½ times a tidal volume of about 1 liter.

Figure 9A:
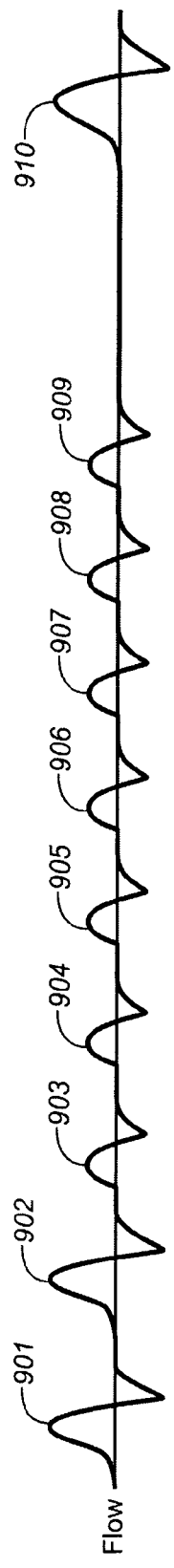
FIGS. 9A to 9D schematically illustrate flow, EMG envelope, lung volume and stimulation respectively in accordance with an aspect of the invention.
Figure 9B:
Figure 9C:
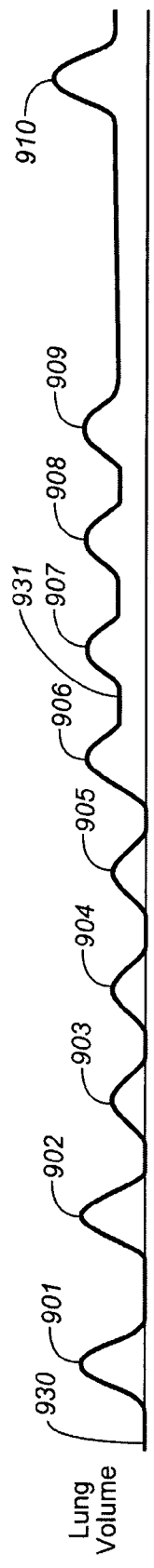
Figure 9D:
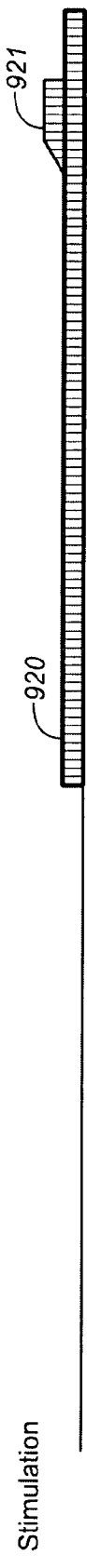

FIG. 9A illustrates a normal flow (FIG. 9A), a normal EMG envelope (FIG. 9B) and normal lung volume (FIG. 9C) at breaths 901, 902 where there is no stimulation (FIG. 9D). Flow is decreasing (FIG. 9A) along with EMG envelope (FIG. 9B) and tidal volume (FIG. 9C) at breaths 903, 904, 905. Reduced flow, EMG and/or lung volume may be detected and may trigger a first stimulation therapy. A low level or bias stimulation 920 (FIG. 9D) is then provided during breaths 906, 907, 908, 909 which results in an increase in functional residual capacity 931 from baseline 930. This increase in functional residual capacity may be therapeutic and may result in resumption of improved drive or breathing from improved gas exchange and/or increased upper airway stability due to an increased functional residual capacity.

After breath 909, a central apnea event occurs. While bias stimulation 920 continues, a paced breath is stimulated 921 to elicit breath 910. Providing bias stimulation before paced breathing or continued during paced breathing may further stabilize the airway during paced breathing. Such paced breathing may continue for a period of time.

Bias stimulation provided before during and/or after other diaphragm stimulation such as breathing control stimulation, augmentation, duty cycle control, paced breathing or other stimulation, for example, as disclosed in co-pending related patent applications set forth herein. Such bias stimulation may reduce a possibility of upper airway closure during the other stimulation.

Bias stimulation may be used in combination with paced breathing or other diaphragm stimulation of respiration, to stabilize the upper airway, and avoid obstructions or the need for tracheotomies in patients who have diaphragm stimulators. For example bias may be used in a diaphragm stimulation device with paralysis patients, ALS patients or other patients who would otherwise need chronic ventilator support.

According to another aspect of the invention a motion sensor or position sensor may be used to determine a patient's position and adjust the stimulation accordingly. For example, therapy may be turned on for a patient with an obstructive disorder where the patient's events are position sensitive. For example the therapy may be turned on when the patient is supine, and the therapy may be turned off when a patient rolls on their side. The stimulation intensity or other parameter may be adjusted depending on a patient's position. The change in position may lead to a change in FRC. Stimulation may be adjusted based on a change in position or a change in FRC. There is also typically a fall in FRC when the patient's state changes from awake to sleep. If this volume change is measured for a patient, it may be used to target a therapeutic volume. For example, the therapeutic volume increase is the same as the FRC fall when the patient goes to sleep.

In accordance with one aspect of the invention, diaphragm stimulation may be combined with Autonomic Nervous System (ANS) or vagal or other parasympathetic activation. In accordance with another aspect of the invention a device for treating apnea having either a component of OSA or CSA by stimulating the diaphragm or phrenic nerve to elicit a diaphragm response, is combined with a vagal stimulation (or other parasympathetic activation caused by electrical stimulation.) For example, diaphragm/phrenic stimulation may cause an increased FRC or biased lung volume, or may modify or control breathing. Neural stimulation to the ANS may also be provided to have an excitatory effect on respiratory drive. Such stimulation may be directly to the central nervous system or to afferents to the central nervous system. Stimulation to one or the other (diaphragm/phrenic or ANS) may be done simultaneously or in an alternating manner. A fully implantable device with multiple leads may be used or external devices may be used or a combination of both. The advantage of combining two types of stimulation, for example, may be that the phrenic nerve stimulation may treat the obstruction or flow limitation by eliciting a mechanical increase in lung volume while the parasympathetic stimulation may help reduce or control sympathetic activation or sympathetic bias that occurs during apnea, to reduce or avoid sharp changes in blood pressure and/or overshooting of respiratory drive that can occur following an apnea.

FIGS. 10A to 10C illustrate an example of an unstable breathing detector and treatment device in accordance with an aspect of the invention. FIG. 10A schematically illustrates output of an audio sensor configured to sense noise or sound associated with snoring. Snoring indicates some degree of airway obstruction and may be correlated to flow limitation. In the example illustrated, as level of snoring increases at breaths 1023, 1024, 1025, a decrease in tidal volume is associated with the snoring (FIG. 10B). Snoring may decrease again (breaths 1026, 1027) and then increase again (breaths 1028, 1029) illustrating instability in breathing and fluctuations in flow and tidal volume. A bias stimulation 1050 is provided at 1040 which provides a decrease (breaths 1030, 1031) in snoring and a normalization or stabilization of an intrinsic normal tidal volume where snoring falls below a detectable level (breaths 1032, 1033 1034).

FIGS. 10A-10C schematically illustrate an effect of stimulation on unstable breathing. While a sensor such as an audio sensor is illustrated. The treatment may alternatively be provided without sensory feedback or with limited sensor feedback for example that indicates an appropriate time for turning on or off therapy for a predetermined period of time or according to a predetermined protocol.

Additionally, while FIGS. 10A-10C illustrate the use of snoring and treatment of snoring as well as treatment of unstable breathing. Other types or forms of unstable breathing or other indications of unstable breathing may be used to identify the presence of unstable breathing. For example, unstable breathing may include an above normal variability in flow, lung volume, tidal volume, breathing rate, minute ventilation, blood gas levels. Such examples may include, those set forth herein and in related applications as set forth herein.

Stimulation in the various embodiments described herein may be patient or clinician activated. For example, a patient may turn a device on before going to sleep. The device may turn on therapy a predetermined time after the patient has turned the device on. The patient may also be provided with an actuation device that delays stimulation when desired, for example for a predetermined period of time. A device may also include sensors or algorithms that turn the device on or off for periods of time, for example during sleep or a particular sleep stage. The device may then provide stimulation according to a predetermined program, for example, intermittently during sleep. Such device may be open loop in that it does not necessarily respond to particular respiratory events. The device may be closed loop in that it senses respiration or other physiological parameters after it has been turned on to respond or adjust based on the parameters. Examples of closed loop detection may include those set forth herein and in related applications as set forth herein.

Stimulation may be triggered on or off by a user or provider, by detection of a patient sleep state. The device may be turned on or off in a number of manners including, e.g., patient turn on followed by delay; patient turn on and an immediate start; turn on based on time of day; turn on or off based on awake/sleep state; or by detection of an event (either onset or resolution). The device may also be turned off upon detection of patient waking up or patient manual deactivation.

The device may be turned on or off, or therapy triggered upon detection of sleep or sleep state. Sleep leads to a number of changes in the body's autonomic function, and physiological parameters. A number of these changes can be detected by the implanted device or external sensors. Activity level can be detected with an implanted or externally attached accelerometer, where a decreased activity can be indicative of sleep. Also, a multidimensional accelerometer can be used to detect that the patient is in a sleep or resting position and turn on/off therapy, or put the device into a "waiting state" for detection of breathing disordered events. In addition, changes in respiratory parameters such as breathing rate, and minute ventilation can be used to detect sleep. For example, baseline respiration rate and minute ventilation can be determined when the patient is in known states, i.e. quiet resting versus sleep. This information could be used to help the device to discriminate between those states. Also the synchrony of respiration with cardiac rhythm changes when going from the wake to the sleep state. This would require a learning algorithm where the device would learn through recording of baseline data the typical synchrony of the respiration versus the heart rate during sleep, and use this information in a sleep detection algorithm. The cardiac rhythm alone can be used to detect sleep as well. For example, histograms could be created for heart rate and heart rate variability in the sleeping and waking state, and these histograms could be used to create reasonable thresholds to allow differentiation between sleep and wake, based on heart rate or heart rate variability.

In addition to individual parameters, the criteria for sleep detection may be a combination of a number of factors, for instance patient indicating that he is laying down and preparing for sleep, time of day, heart and respiratory rate or pattern. When two or more of the criteria are met the device may determine that the patient was asleep.

In addition to differentiating between in sleep and awake state, the device may differentiate between different stages of sleep. The stages of sleep include Stage 1, a transitional stage, Stage 2, a light sleep state, Stage 3 and 4, slow wave or deep sleep, and REM, or rapid eye movement sleep, where dreaming, muscle paralysis, and a lot of variability in sympathetic tone occur. Patients vary according to which sleep stage most of their disordered breathing occurs. But in most patients, REM sleep is where a majority of OSA episodes occur due to the reduced functioning of the upper airway muscles, and stage 3 and 4 are relatively free of breathing disordered events. Therefore it may be advantageous for the device to turn on or adjust therapy to a higher level at the detection of REM sleep, and turn off or reduce therapy at detection of stage 3 and 4 sleep.

While the invention has been described in detail with reference to preferred embodiments thereof, it will be apparent to one skilled in the art that various changes can be made, and equivalents employed, without departing from the scope of the invention.

The invention claimed is:
1. A method for treating a subject comprising the steps of:
   sensing one or more characteristics of breathing;
   detecting flow limited breathing from the sensed one or more characteristics of breathing and recording information relating to the flow limited breathing via polysomnography, wherein detecting flow limited breathing comprises sensing an EMG complex of the subject's diaphragm and detecting flow limited breathing from a determination of a parameter corresponding to an area under a power spectral density plot of the EMG complex;
   identifying at least one cause of the flow limited breathing based on the recorded information;
   correlating the at least one cause to an electrical stimulation protocol programmed to treat the flow limited breathing; and
   providing electrical stimulation during an existing respiratory cycle according to the protocol to elicit a diaphragm response to thereby reduce flow limited breathing.
2. The method of claim 1 wherein the step of detecting flow limited breathing from the sensed one or more characteristic of breathing comprises:
   detecting a diaphragm EMG having one or more components corresponding to flow limited breathing.

3. The method of claim 2 wherein the step of detecting flow limited breathing from the sensed one or more characteristic of breathing comprises:
detecting a diaphragm EMG complex having a frequency content corresponding to flow limited breathing.

4. The method of claim 2 wherein the step of detecting flow limited breathing from the sensed one or more characteristic of breathing comprises:
detecting a diaphragm EMG envelope having a flattened morphology corresponding to flow limited breathing.

5. The method of claim 2 wherein the step of detecting flow limited breathing from the sensed one or more characteristic of breathing comprises:
detecting a diaphragm EMG complex having an increased width corresponding to flow limited breathing.

6. The method of claim 1 wherein the step of detecting flow limited breathing from at least one EMG parameter comprises:
detecting a diaphragm EMG complex having an increased density of spikes corresponding to flow limited breathing.

7. The method of claim 1 wherein the step of detecting flow limited breathing from at least one EMG parameter comprises:
detecting a diaphragm EMG complex having an increased rising slope corresponding to flow limited breathing.

8. The method of claim 2 wherein the step of detecting flow limited breathing from the sensed one or more characteristic of breathing comprises:
detecting a diaphragm EMG complex having an increased amplitudes of a plurality of corresponding to flow limited breathing.

9. The method of claim 1 wherein the step of providing electrical stimulation according to the protocol to elicit a diaphragm contraction response comprises providing electrical stimulation to increase a baseline lung volume.

10. The method of claim 1 wherein the step of providing electrical stimulation according to the protocol to elicit a diaphragm contraction response comprises providing electrical stimulation to manipulate inspiration duration with respect to duration of a corresponding respiratory cycle.

11. The method of claim 1 wherein the step of providing electrical stimulation according to the protocol to elicit a diaphragm contraction response comprises providing electrical stimulation to inhibit central respiratory drive and to provide therapeutic breathing control.

12. The method of claim 1 wherein the step of providing electrical stimulation according to the protocol to elicit a diaphragm contraction response comprises providing electrical stimulation to manipulate tidal volume.

13. The method of claim 1 further comprising the steps of detecting an imminent disordered event and adjusting the stimulation in response.

14. The method of claim 13 wherein the step of detecting an imminent disordered event comprises detecting a physiological parameter corresponding to a precursor to onset of a disordered event; and wherein the step of adjusting stimulation comprises providing a stimulation directed to preventing onset of the disordered event.

15. The method of claim 14 wherein the step of providing a stimulation directed to preventing onset of the disordered event comprises providing stimulation to elicit a lung volume bias.

16. The method of claim 1 further comprising the steps of detecting onset of a disordered event and adjusting the stimulation in response.

17. The method of claim 16 wherein the step of detecting onset of a disordered event comprises detecting an airway obstruction; and wherein the step of adjusting stimulation comprises turning off stimulation.

18. The method of claim 16 wherein the step of detecting onset of a disordered event comprises detecting central apnea; and wherein the step of adjusting stimulation comprises delivering paced breathing stimulation.

19. The method of claim 1 further comprising setting a detection level for flow limited breathing based on data from the patient.

20. The method of claim 1 further comprising setting a detection level for flow limited breathing based on a degree of flow limitation.

21. The method of claim 1 further comprising setting a detection level for flow limited breathing based on a number of flow limited episodes that are observed in a period of time.

22. The method of claim 1 wherein identifying at least one cause comprises identifying a reduction in a central respiratory drive.

23. The method of claim 22 wherein providing electrical stimulation according to the protocol comprises applying the electrical stimulation to phrenic nerve or diaphragm tissue to supplement or augment at least one breath.

24. The method of claim 1 wherein identifying at least one cause comprises identifying a reduction in lung volume.

25. The method of claim 24 wherein providing electrical stimulation according to the protocol comprises applying the electrical stimulation to phrenic nerve or diaphragm tissue during an exhalation.

26. The method of claim 1 wherein identifying at least one cause comprises identifying an episode of central sleep apnea.

27. The method of claim 26 wherein providing electrical stimulation according to the protocol comprises applying the electrical stimulation to phrenic nerve or diaphragm tissue such that the breathing is paced.

28. The method of claim 1 wherein identifying at least one cause comprises identifying an episode of Cheyne-Stokes.

29. The method of claim 28 wherein providing electrical stimulation according to the protocol comprises applying the electrical stimulation to phrenic nerve or diaphragm tissue to supplement a breath.

30. The method of claim 1 wherein identifying at least one cause comprises identifying an episode of hypopnea.

31. The method of claim 1 wherein identifying at least one cause comprises identifying an episode of obstructive sleep apnea.

32. The method of claim 31 wherein providing electrical stimulation according to the protocol comprises applying the electrical stimulation to phrenic nerve or diaphragm tissue to maintain airway patency.

33. The method of claim 1 wherein the step of correlating the at least one cause to an electrical stimulation protocol further comprises defining a type of the electrical stimulation based upon the information from polysomnography.

34. The method of claim 1 wherein the step of correlating the at least one cause to an electrical stimulation protocol further comprises determining one or more stimulation parameters of the electrical stimulation based upon the information from polysomnography.

35. The method of claim 1 further comprising sensing one or more physiological parameters of the subject.

36. The method of claim 35 where the physiological parameters comprise ECG, heart rate, or heart rate variability.

37. A method for detecting a flow limitation comprising the steps of:
sensing EMG of a subject's diaphragm;
detecting a flow limitation from at least one EMG parameter wherein the at least one EMG parameter comprises a frequency content of an EMG complex;
recording the EMG parameter relating to the flow limitation via polysomnography;
identifying at least one cause of the flow limitation based on the recorded EMG parameter from a determination of the EMG parameter corresponding to an area under a power spectral density plot of the EMG complex;
correlating the at least one cause to an electrical stimulation protocol programmed to treat the flow limited breathing; and
providing electrical stimulation according to the protocol to elicit a diaphragm response to thereby reduce flow limitation.

38. The method of claim 37 wherein the step of detecting the flow limitation comprises detecting flow limited breathing.

39. The method of claim 37 wherein the step of detecting the flow limitation comprises detecting an airway obstruction.

40. The method of claim 37 wherein the step of detecting the flow limitation from at least one EMG parameter further comprises:
detecting a diaphragm EMG envelope having a flattened morphology corresponding to a flow limited breathing.

41. The method of claim 37 wherein the step of detecting the flow limitation from at least one EMG parameter further comprises:
detecting a diaphragm EMG complex having an increased width corresponding to flow limited breathing.

42. The method of claim 37 wherein the step of detecting the flow limitation from at least one EMG parameter further comprises:
detecting a diaphragm EMG complex having an increased amplitudes of a plurality of spikes corresponding to flow limited breathing.

43. The method of claim 37 wherein the step of detecting the flow limitation from at least one EMG parameter further comprises:
detecting a diaphragm EMG complex having an increased density of spikes corresponding to flow limited breathing.

44. The method of claim 37 wherein the step of detecting the flow limitation from at least one EMG parameter comprises:
detecting a diaphragm EMG complex having an increased rising slope corresponding to flow limited breathing.

45. The method of claim 37 wherein the step of correlating the at least one cause to an electrical stimulation protocol further comprises defining a type of the electrical stimulation based upon the information from polysomnography.

46. The method of claim 37 wherein the step of correlating the at least one cause to an electrical stimulation protocol further comprises determining one or more stimulation parameters of the electrical stimulation based upon the information from polysomnography.

47. The method of claim 37 further comprising sensing one or more physiological parameters of the subject.

48. The method of claim 47 where the physiological parameters comprise ECG, heart rate, or heart rate variability.

* * * * *